US010517800B2

(12) United States Patent
Tatarek et al.

(10) Patent No.: US 10,517,800 B2
(45) Date of Patent: Dec. 31, 2019

(54) NASAL BRIDLE INSERTION DEVICE

(71) Applicant: T & T Devices Ltd, Hampshire (GB)

(72) Inventors: Andrew Tatarek, Hampshire (GB); Stephen John Taylor, Bristol (GB)

(73) Assignee: T & T DEVICES LTD, Hampshire (GB)

( * ) Notice: Subject to any disclaimer, the term of this patent is extended or adjusted under 35 U.S.C. 154(b) by 73 days.

(21) Appl. No.: 15/128,833

(22) PCT Filed: Mar. 24, 2015

(86) PCT No.: PCT/GB2015/050877
§ 371 (c)(1),
(2) Date: Sep. 23, 2016

(87) PCT Pub. No.: WO2015/145137
PCT Pub. Date: Oct. 1, 2015

(65) Prior Publication Data
US 2017/0105904 A1    Apr. 20, 2017

(30) Foreign Application Priority Data
Mar. 24, 2014   (GB) ................... 1405244.3

(51) Int. Cl.
*A61J 15/00*   (2006.01)
*A61B 17/24*   (2006.01)
(Continued)

(52) U.S. Cl.
CPC .......... *A61J 15/0061* (2013.01); *A61B 17/24* (2013.01); *A61J 15/0003* (2013.01);
(Continued)

(58) Field of Classification Search
CPC .......... A61M 16/0461; A61M 16/0488; A61M 16/0666; A61M 16/0672; A61M 25/0138;
(Continued)

(56) References Cited

U.S. PATENT DOCUMENTS 5,185,005 A    2/1993  Ballantyne
5,300,048 A *  4/1994  Drewes, Jr. ....... A61M 25/0108
                                                       600/435
(Continued)

FOREIGN PATENT DOCUMENTS

WO    2014109846 A1    7/2014

OTHER PUBLICATIONS

NPSA. Patient Safety Alert NPSA/2011/PSA002: Reducing the harm caused by misplaced nasogastric feeding tubes in adults, children and infants. Supporting Information. Mar. 2011.

(Continued)

*Primary Examiner* — Kami A Bosworth
(74) *Attorney, Agent, or Firm* — Volpe and Koenig, P.C.

(57) ABSTRACT

A device to assist with the insertion of a nasal bridle includes an insertion guide and an introducer that is attached to bridle tape. The guide is switchable between two configurations: a substantially straight configuration and a second configuration in which an exit aperture at an upper end of the guide is either at a downwardly oriented angle and/or displaced laterally from the guide longitudinal axis, for example by causing the upper end of the guide to adopt a u-bend. The guide is inserted into a nostril while straight and then adopts its second configuration. The introducer is pushed through the guide and, at the exit, is guided beyond the septum into and out of the opposite nostril. Introducer and tape are pulled through the nasal passage before removing the guide. The guide therefore ensures that introducer and tape are held clear of the septum, reducing discomfort.

15 Claims, 12 Drawing Sheets

(51) Int. Cl.
*A61M 16/04* (2006.01)
*A61B 17/00* (2006.01)

(52) U.S. Cl.
CPC .... *A61M 16/0461* (2013.01); *A61M 16/0488* (2013.01); *A61B 2017/00309* (2013.01); *A61B 2017/00455* (2013.01)

(58) Field of Classification Search
CPC .......... A61M 25/0147; A61M 25/0152; A61M 2025/0163; A61M 2025/0226; A61M 2010/0618; A61M 2210/0618; A61M 25/0102; A61J 15/0003; A61J 15/0007; A61J 15/0026; A61J 15/0053–0065
See application file for complete search history.

(56) References Cited

U.S. PATENT DOCUMENTS

| | | | |
|---|---|---|---|
| 5,458,585 A * | 10/1995 | Salmon | A61B 8/12 600/467 |
| 5,885,288 A * | 3/1999 | Aust | A61B 17/29 604/22 |
| 6,464,668 B1 | 10/2002 | Pace | |
| 6,631,715 B2 | 10/2003 | Kirn | |
| 2002/0026936 A1 | 3/2002 | Kirn et al. | |
| 2005/0236001 A1 * | 10/2005 | Williams | A61M 25/02 128/207.18 |
| 2005/0256452 A1 * | 11/2005 | DeMarchi | A61M 25/0017 604/95.04 |
| 2006/0095066 A1 | 5/2006 | Chang et al. | |
| 2012/0071857 A1 | 3/2012 | Goldfarb et al. | |
| 2012/0239050 A1 | 9/2012 | Linderman et al. | |
| 2013/0338521 A1 * | 12/2013 | Thompson | A61M 39/08 600/532 |
| 2014/0018732 A1 | 1/2014 | Bagaoisan et al. | |
| 2014/0041666 A1 | 2/2014 | Slaga et al. | |
| 2014/0088355 A1 * | 3/2014 | Schaeffer | A61M 25/0136 600/109 |
| 2015/0157828 A1 * | 6/2015 | Phillips | A61M 16/0497 604/95.01 |

OTHER PUBLICATIONS

Seder CW, Stockdale W, Hale L, Janczyk RJ. Nasal bridling decreases feeding tube dislodgment and may increase caloric intake in the surgical intensive care unit: a randomized, controlled trial. Critical Care Medicine. 2010;38:797-801.
Sparks DA, Chase DM, Coughlin LM, Perry E. Pulmonary Complications of 9931 Narrow-Bore Nasoenteric Tubes During Blind Placement: A Critical Review. Journal of Parenteral and Enteral Nurition. 2011;35:625-629.
Taylor SJ. Confirming nasogastric feeding tube position versus the need to feed. Intensive and Critical Care Nursing. 2013; 29: 59-69.
Taylor SJ, Allan K. McWilliam H, Brown J, Manara A. Equivalnce of electromagnetic tracing (Cortrak) to X-ray in confirming position of nasogastric tube position.2014. Submitted for journal review.

* cited by examiner

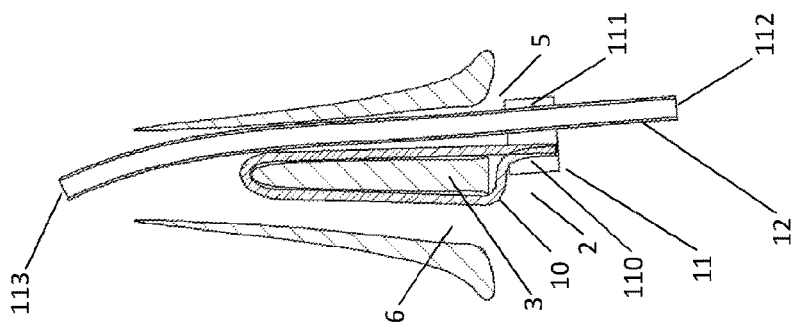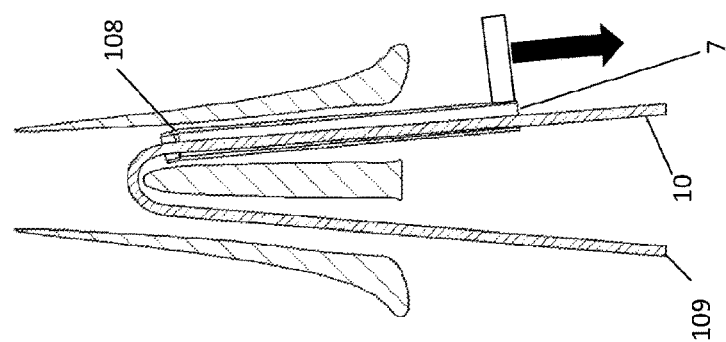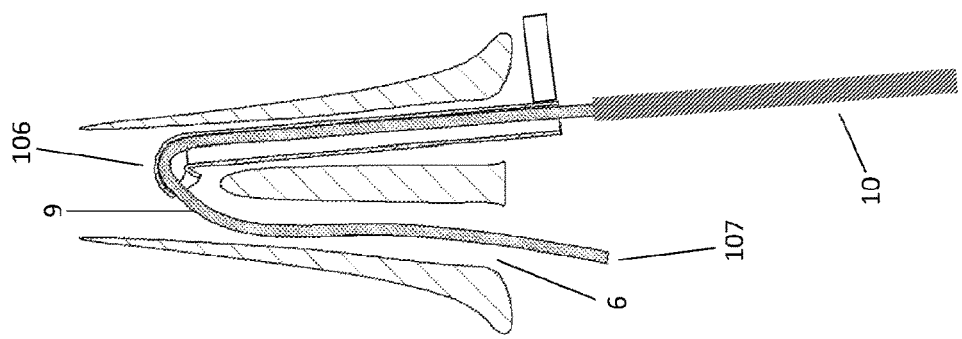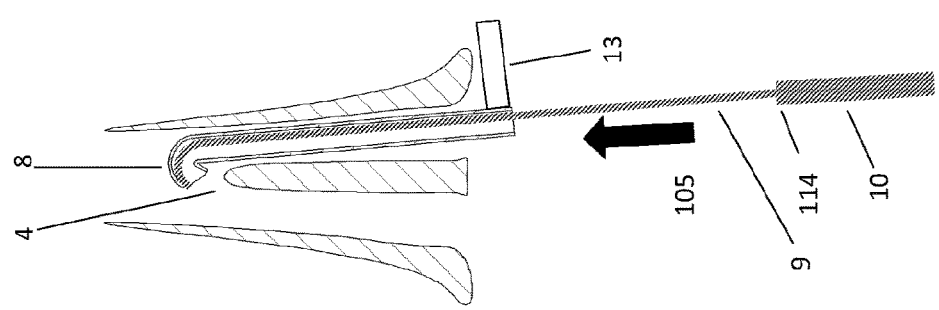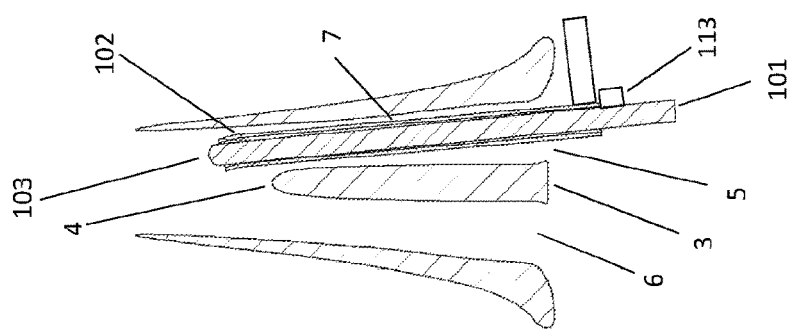

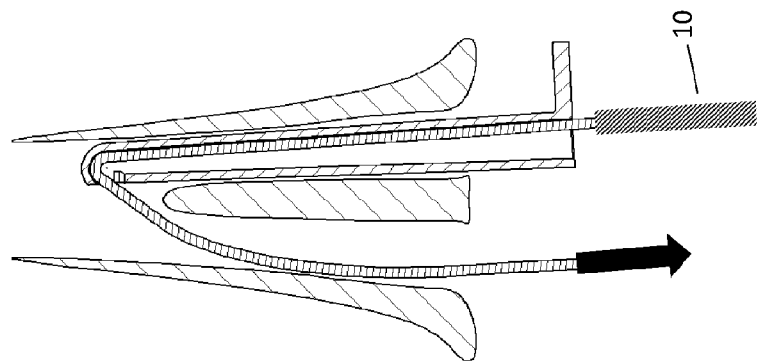
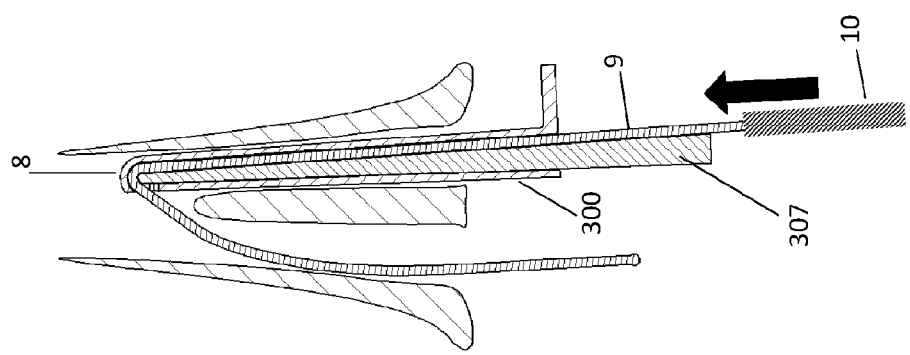
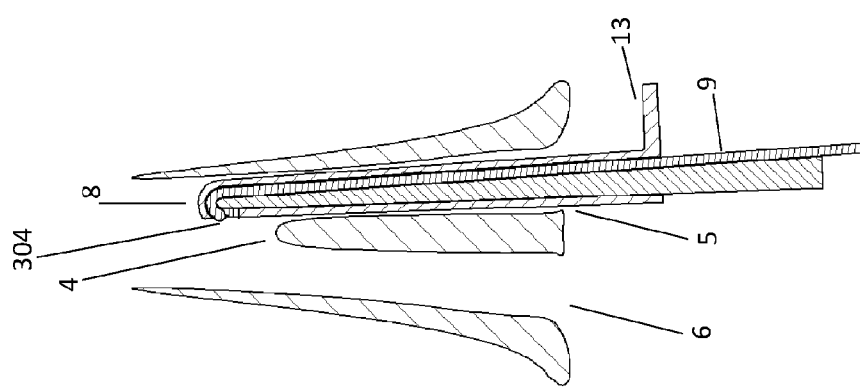
Fig 3c
Fig 3b
Fig 3a

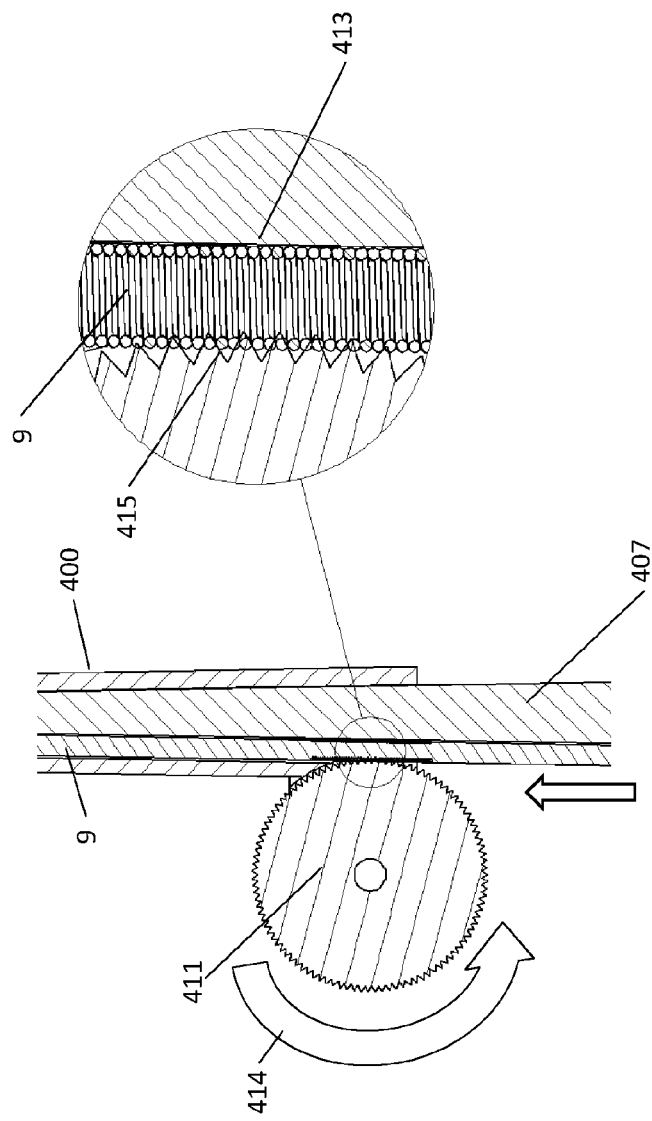
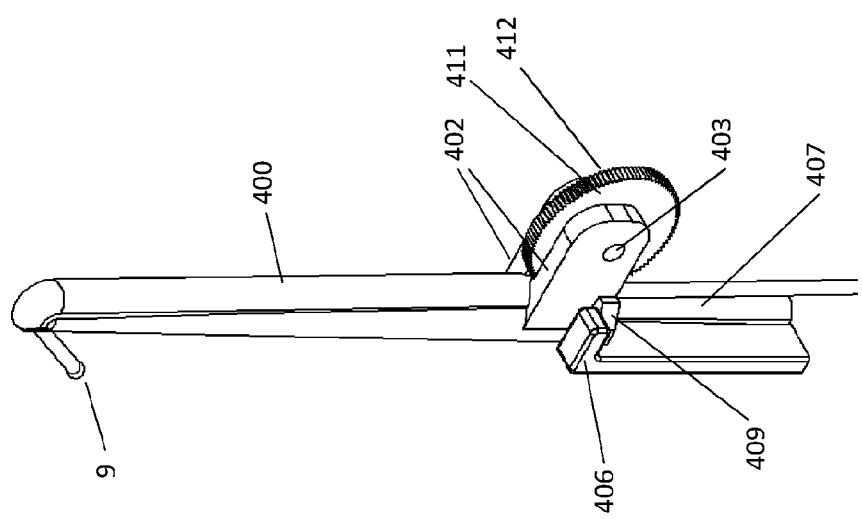
Fig 4b
Fig 4a

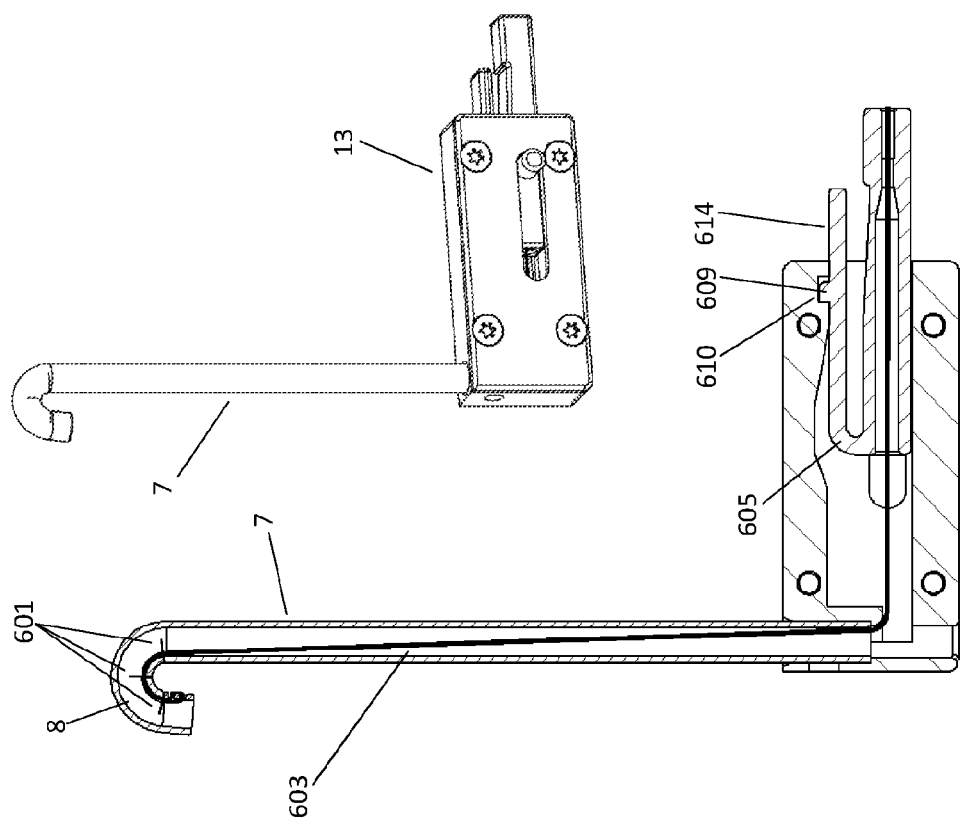
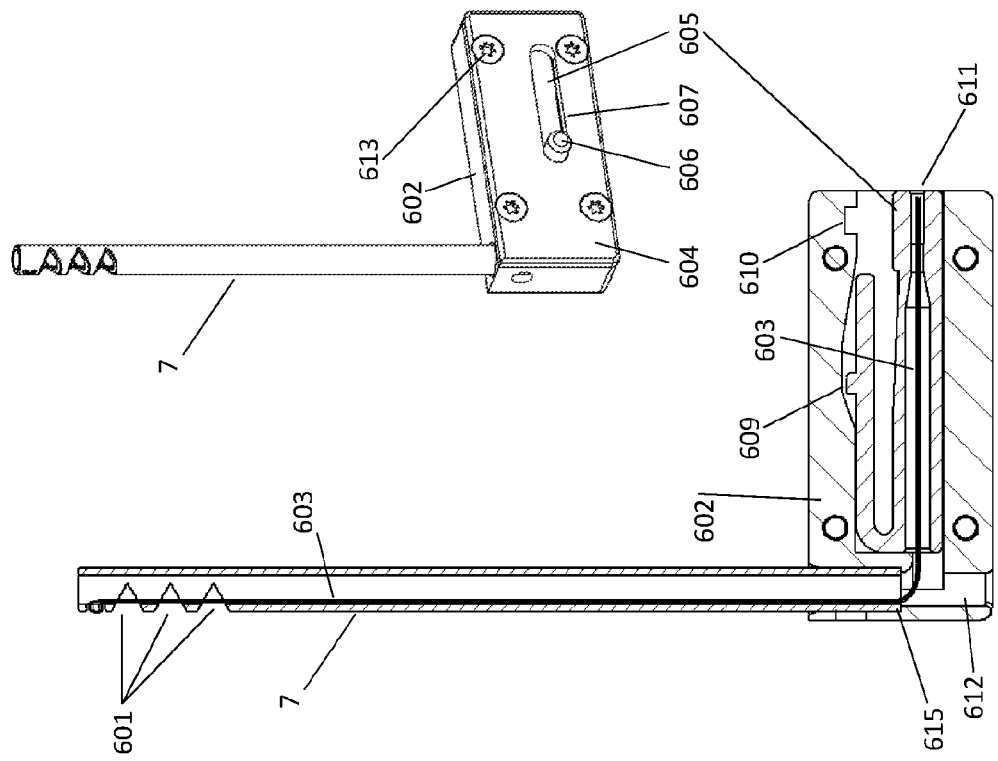

NASAL BRIDLE INSERTION DEVICE

The present invention relates to the field of feeding tubes, which are used to maintain the nutrition of a hospital patient unable to feed themselves. In particular, this invention relates to a device to assist with the fitting of a nasal bridle to which the feeding tube is to be attached. It also relates to a method of fitting the nasal bridle.

Although nasal feeding is the primary field of application of the present invention, this is not to be seen as unduly limiting. Other tubes, for example a nasotracheal tube, are also required to be passed through the nose and positioned internally within a patient. Such tubes can also benefit from being held in position by a nasal bridle and so this invention is equally applicable to systems for placing and securing other forms of nasal tube. It is expected though to be used more frequently in the placement of feeding tubes.

Approximately 5% of hospital patients require tube feeding to maintain their nutrition. Without adequate nutrition, the cost of treating disease increases, along with the risk of complications, and even death. Most short-term tube feeding is done via tubes inserted through the nose and into the stomach (nasogastric, NG) or intestine (nasointestinal, NI).

Insertion of a feeding tube is however an invasive procedure that involves a varying degree of discomfort and risk for the patient. Infection or trauma may occur during insertion if the tube accidentally enters the lung. A misplaced tube carries bacteria from the nasopharynx into the lung, potentially causing pneumonia. It may also puncture the lung through pressure on membranes. Moreover, if a misplaced tube remains undetected, the nutrition will be delivered to the lung. The UK officially records 20 undetected misplacement events per year leading to 4 deaths [NPSA, 2011]. However, the actual figure may far higher [Sparks et al, 2011; Taylor, 2013a]. In order to reduce the chance of misplacement, X-ray imaging is used to confirm tube position during insertion. This though, increases patient exposure to x-rays.

Exact figures are lacking but several million tubes are placed worldwide and one study suggests misplacement occurs in 1.5% of placements; pneumonia and/or lung puncture in 0.5%; and 0.27% kill [Taylor, 2014].

In addition to the risk of misplacement, most tubes are actually lost before the requirement for them is over. The patient may inadvertently pull the tube out (46%) or it may simply slip out (6%) [Taylor et al, 2014]. In the vast majority of these cases, tube replacement is necessary, thereby repeatedly incurring the risks cited above. Inadvertent tube removal occurs predominantly in patients with depressed consciousness [Sorokin and Gottlieb, 2006]. Tube loss is common because most tubes are secured by some form of taping that easily comes loose or is removed. In addition to direct risks arising from additional tube placements, delays in replacement lead to cumulative malnutrition and consequent complications.

In all cases, the need to replace tubes, and the complications associated with the procedure, increase healthcare cost.

In order to reduce the likelihood of loss, a nasal bridle may be used to hold a feeding tube in place. A nasal bridle comprises a loop of tubing or surgical tape that is placed around the nasal septum and attached to the feeding tube. Tape (in modern devices) is inserted up one nostril, around the back of the septum and down the opposite nostril. The two ends are joined together at the front of the septum to form a secure attachment point to the patient. The feeding tube is attached to the nasal bridle, greatly reducing risk of inadvertent removal.

Nasal bridles are found to reduce tube dislodgement from 63% to 18% [Seder et al, 2010]. This makes them clinically very useful, with many consequential benefits. The exposure of patients to X-rays is reduced, as re-insertion generally requires the use of X-rays to check tube position [Gupta et al, 2010]. The nutritional energy delivered as a percentage of the target is increased: 62% to 78% [Seder et al, 2010]. Inadvertent tube removal occurs less often and so the patient is fed for a larger percentage of the prescribed feeding time. This reduces risk and cost of malnutrition. The cost of staff time in replacing tubes is reduced. The reduction in the number of insertions gives rise to a corresponding reduction in the risks, both clinical and litigious, associated with tube misplacement. It is estimated that if all patients were fitted with a nasal bridle it would reduce the number of tubes placed, and their proportionate risks, by 31% [Taylor, 2014].

Unfortunately most methods used to insert a nasal bridle employ equipment that is not specifically designed for the purpose. The procedure can be extremely uncomfortable for the patient. The most common method entails placing one feeding tube through each nostril into the throat (nasopharynx), using forceps to pull the feeding tubes out of the mouth, attaching the tubes together, then pulling on one tube so that the other is pulled around the back of the septum and out of the opposite nostril. The two ends of this tube are now sticking out of each nostril and are cut to length and fixed together using adhesive tape, knot or suture to form a bridle. The actual feeding tube is then anchored to this, the nasal bridle.

In addition to the discomfort to the patient, this procedure is time-consuming and expensive in feeding tubes. Moreover securing the feeding tube to the nasal bridle is difficult because there is no purpose-made attachment point and both this and the bridle per se may come undone, allowing the tube to be pulled out.

A device developed by AMT and intended specifically for use as a nasal bridle is described in U.S. Pat. No. 6,631,715 B2. This device consists of a 2-piece introducer, each piece with a rare-earth magnet at the tip. One piece is inserted into each nostril, such that the magnets connect behind the septum. A stiffener (obdurator) is then removed from one introducer, with the result that when the opposing introducer is pulled, the unstiffened part is drawn behind the septum and out of the opposing nostril.

Although representing an undoubted improvement, there remain many disadvantages with this prior art device. First, the insertion procedure can still be uncomfortable and risks damage to the septum. Blind insertion and connection of the magnets behind the septum can be difficult to achieve; and is made more difficult if there is an existing tube in place. Once connected, the bridle tape must still be pulled through from one nostril to the other, without support. This directly 'frictions' and risks damage to the septum. Cost is also an issue: rare-earth magnets are relatively expensive, and often difficult to source, making the device expensive and uneconomical for universal use. Further, the magnets have to be very securely attached and can be harmful if they become detached inside the patient and are swallowed. Finally, the clips in this prior art device are single use only. If therefore a feeding tube needs to be replaced, for example if it becomes blocked, then the bridle tape must be cut and the bridle discarded and replaced. This means that a new introducer has to be used if a tube is to be replaced, adding to patient discomfort and healthcare cost.

There is accordingly a perceived need for an alternative method of inserting a nasal bridle. It is an object of the present invention to provide an insertion device to fit a nasal bridle to a patient with reduced discomfort and cost than is currently available in the prior art.

The present invention provides a device to assist with insertion of a nasal bridle, the device being in the form of an elongated insertion guide made of flexible resilient material of a size suitable for insertion in a nasal passage, the guide being switchable between two configurations and comprising a tip portion that includes an exit aperture, wherein when the guide is arranged in an introduction configuration, either the exit aperture is downwardly oriented at an angle to the guide longitudinal direction and/or displaced laterally from the guide longitudinal direction such that when the guide is inserted in a first nasal passage and the aperture positioned above a nasal septum, an introducer exiting the aperture is guided beyond the septum into the second nasal passage.

This novel design of apparatus creates a u-bend behind the septum to guide an introducer inserted into the insertion guide out of the opposite nostril. The introducer is attached to a length of bridle tape, which is accordingly also pulled through the nostrils, following the path of the introducer. Creating the u-bend is important as it ensures that the introducer is held above the septum, minimising the risk of discomfort as both this and the bridle tape are pulled through. Once the tape is threaded around the septum, the insertion guide may be withdrawn, leaving the two ends of the loop of bridle tape protruding from respective nostrils. A bridle connector may then be fitted to the free ends of bridle tape, creating an anchor point for attaching a feeding tube to the nasal bridle.

This device of the present invention is considerably less costly than the prior art insertion device, which relies on rare earth magnets. It is also presents less discomfort to the patient, in comparison both with the magnet device and other insertion methods in which no device assistance is used.

The guide is preferably switchable between an insertion configuration and the introduction configuration by means of an adjustment to the tip such that in the insertion configuration the tip is substantially straight, in line with the guide longitudinal direction and in the introduction configuration, the tip is hooked.

This arrangement is advantageous in that is satisfies two conflicting requirements: the need for the introducer to be guided around the septum and the need to keep the cross-sectional profile small in order to minimise discomfort during insertion. In this embodiment, this is achieved by a design of guide in which both configurations are possible, and which can be adopted according to requirements. That is, the profile is kept low during insertion and the hooked tip ensures passage of the introducer and bridle tape over the septum during introduction.

It a preferred embodiment, one side of the tip includes one or more wedged slits. A tensionable actuation lead is attached to the same side of the tip at or beyond the slits, such that tensioning the actuation lead closes the slits, causing the tip to adopt its hooked, introduction configuration. This arrangement provides a convenient mechanism by which switching between the two required configurations may be achieved.

The guide may comprise two parts: an upper flexible end, which includes the tip and a lower shaft portion, the upper flexible end being fabricated from a softer, more flexible material than the lower shaft portion. Specifically, the upper flexible end may fabricated from a thermoplastic elastomer (TPE), a thermoplastic polyurethane material, rubber or low-density polyethylene. The lower shaft portion may fabricated from a harder TPE, polypropylene, polyethylene or other similar plastic. The separation of the guide into two parts, allows different materials to be used for each part: a more flexible softer material for the tip, which is required to flex around the u-bend and is more likely to cause damage to the nasal passage during guide insertion; and a stiffer, less flexible material for the shaft of the guide. This arrangement is further advantageous in that it permits the guide to be manufactured by moulding. This is a highly desirable fabrication process in that it allows the shape of the moulded part to be very tightly controlled, ensuring that all edges are smooth so as to cause minimal trauma to a patient when the device is being used. If a single-material guide is used, the flexibility requirement is incompatible with moulding such an elongate structure.

The introducer can be a wire, a spring, a tube, or other suitable material that fits inside the insertion guide. The introducer is advantageously constructed as thin as possible so that the insertion guide can be as small as possible. The join between the introducer and the bridle tape is made with minimal thickness to the same end, and the present invention provides ways to achieve this.

In preferred embodiments, the device also includes an actuator switch with clip connected to the tensionable actuation lead, wherein the clip is moveable between a first position in which the actuation lead is substantially free from tension and a second position in which it is under tension, the tension being sufficient to cause the tip to adopt its hooked introduction configuration. Alternatively, the clip may be moveable through a range of positions, each of which imparts a different tension to the actuation lead, thereby enabling selection of a range of introduction configurations. This clip itself provides a simply-operated external mechanism to control the configuration adopted by the insertion guide. Allowing it to apply a discrete range of tensions in turn permits the orientation angle of the exit aperture to be adjusted in accordance with the physiology of the patient.

The actuator switch may be affixed to a proximal end of the insertion guide, remote from the tip. It may further include a passage which is substantially in line with the longitudinal axis of the insertion guide. This is a convenient arrangement by which it ensures that the actuator switch does not interfere with the more fundamental requirement of enabling the introducer to pass along the guide. Another advantage of the actuator switch is that its housing may be fixed in a particular orientation in relation to the exit aperture. This allows the switch housing, which remains outside the nostril, to be used to provide an indication of exit aperture orientation when the guide is fully inserted into the nostril.

In a particularly preferred embodiment, the housing and lower shaft portion are of unitary construction. They may therefore be conveniently moulded as a single part.

The device may also include an orientation indicator in the form of a finger, shaft or other protrusion that extends radially outwardly from a position towards the lower end of the guide in a direction that is fixed in relation to the location of the exit aperture. This protrusion, being at the guide's lower end, remains outside the nostril when the insertion guide is in use. It therefore provides an external indication of the orientation of the exit aperture, which is hidden within the nostril. This feature will accordingly allow a clinician using the insertion device to align the exit aperture to face towards and behind the nasal septum and so the introducer will be directed out and down the opposite nostril. Ideally, the orientation indicator extends in a direction opposite to a side of the guide that includes the exit aperture. This keeps it from obstructing the clear nostril and hindering the patient's breathing. Alternatively, a simple form of marking on the insertion guide surface may also function as an orientation indicator.

In an alternative embodiment, the guide is hooked at its tip and adapted to receive an insert made of stiffer material such that the insertion configuration is achieved by location of the insert along the length of the guide to straighten the tip.

In a further alternative embodiment, the exit aperture is located to one side of the guide tip and the guide comprises a main passage and an adjacent passage extending therethrough, the main passage being adapted to receive an inner guide core such that, when the core is fully inserted into the guide, the guide is in its introduction configuration with a hooked passage extending from the adjacent passage above the inner guide core to the exit aperture. This alternative arrangement provides another low-profile guide.

The insertion guide may include a drive means, such as a cogged wheel, to help push the introducer around the guide channel. This feature is particularly advantageous if the bend at the top is tight.

In a second aspect, the present invention provides an introducer for use with the insertion guide described above. The introducer comprises a core wire surrounded by a cylindrical shape of stiffer construction, the core wire having a smooth shape on its leading end, which protrudes from the cylindrical shape, and is attached with a low-profile join at its trailing end to a length of bridle tape.

Such an introducer ideally consists of a length of material that is sufficiently stiff to allow it to be pushed through the insertion guide (with bridle tape attached), and to find its way down the opposite nostril while being pushed. On the other hand, it should be sufficiently flexible to bend round the top of the insertion guide.

Once pushed through sufficiently to be protruding from the opposite nostril, the introducer is pulled through, with bridle tape following.

The introducer may advantageously consist of a length of fine tightly wound spring, such that it is flexible to allow travel around the bend at the top of the insertion guide, but rigid to allow it to be pushed up the channel of the insertion guide. It should also be of sufficient length such that it is able to emerge more than 2 cm from the opposite nostril, while still being pushed into the insertion guide.

The introducer may include an internal stiffener along part or all of its length to make it more rigid, particularly when being pushed down the opposite nostril.

The introducer (if it is a spring) may include a length of wire or strong thread inside it, along its whole length, attached at the front, and at the back, to prevent the spring wire stretching and the stretched wire cutting the septum.

The bridle tape may be attached to the introducer by any of the common methods of attachment, such as adhesive, heat shrink, ultrasonic welding, etc. with the join being smooth, to minimise friction when being pulled through.

The bridle tape may be attached to the introducer by a loop of wire or thread. Both ends of the loop are threaded through the introducer, a bridle tape is then threaded through the loop, the free ends of the wire or thread are pulled tight and fastened at the front end of the introducer e.g. by knotting, adhesive or other means. In this way, the bridle tape is held tightly by the loop.

If the introducer is constructed as a tightly wound spring, the proximal end of the inserter may be slightly expanded, so that the bridle tape end can be attached and tucked inside the expanded end, in order to present a smooth join when being pulled through.

The introducer may include a smooth, substantially spherical bead, for example of plastic or cured adhesive, at the leading end. This improves its ability to deflect off obstructions and continue its advance. It also reduces risk of membrane trauma.

The end of the introducer may be slightly bent, a short distance from the leading end, making it possible to get around obstacles by turning it and pushing.

The introducer and the insertion guide may be lubricated to reduce friction between the parts and assist easy movement through the nostril.

In some embodiments, the present invention also includes a bridle connector, able to be attached to the two ends of the bridle tape protruding from respective nostrils after insertion, and providing means for attaching one or more feeding tubes.

The bridle connector may advantageously connect to the two ends of the bridle tape after they are looped over the septum. The bridle connector further may include means to attach to one or more feeding tube(s), inserted into one or both nostrils and attached securely enough to prevent inadvertent removal of the feeding tube(s). The bridle connector may include means to allow deliberate detachment and re-attachment by a clinician, should a feeding tube require to be removed or replaced and the replacement re-attached to the bridle. This obviates the need to reinsert the bridle if the tube needs to be replaced.

Advantageously the bridle connector may connect in a secure and permanent way to the two ends of the bridle tape, such that the only way to remove the nasal bridle is to cut the bridle tape.

Alternatively the bridle connector may detach from the bridle tape and be replaced for attachment or replacement of feeding tubes.

In other embodiments, the present invention may also include driving means to advance the introducer. Such a driving means may consist of a wheel connected to the insertion guide. The wheel's outer surface may be characterised by high friction in its contact with the introducer. This may be achieved, for example, by providing it with a high friction elastomeric surface, such as rubber, or with fine gear teeth that mesh with the introducer. When the wheel is rotated, contact between the wheel and the introducer causes the introducer to move substantially the same amount as the outer diameter of the wheel.

For use with such a driving wheel, the surface of the insertion guide contacting the introducer opposite to the contact point of the driving wheel may be arranged to be of relatively low friction against the introducer, such that it does not impede the movement imparted by the driving wheel to the introducer. To this end, the internal surface of the introducer may be lubricated.

The nasal bridle insertion device may be presented to the clinician with the introducer already placed in the insertion guide, with the lead-end of the introducer in the exit hole, and the inner core in place, so that it is ready to be passed into the nose and operated with minimum clinician effort.

The outside of the insertion guide may include markings to indicate how far it is inserted, to assist the clinician in dealing with different septum lengths.

In another aspect, the present invention provides a method of inserting a nasal bridle into a nose, the method comprising:

(a) Inserting into a first nasal passage an elongated insertion guide made of flexible resilient material with a tip portion that includes an exit aperture, until the exit aperture is positioned above the septum;

(b) Ensuring that the exit aperture is oriented downwardly at an angle to a longitudinal direction of the guide or laterally displaced from the longitudinal direction, either by pre-configuring the guide or by causing the guide, in situ, to adopt an introduction configuration with hooked tip;

(c) Threading an introducer, attached to a nasal bridle tape, out of the exit aperture via the hooked tip such that it is directed around the septum into a second nasal passage until the introducer emerges from the second nasal passage;

(d) Pulling the introducer out through the second nostril until the nasal bridle tape emerges; and (e) Removing the insertion guide.

In order that the present invention may be better understood, embodiments thereof, which are given by way of example only, will now be described with reference to the accompanying drawings.

Throughout the figures a simple representation of the nostrils and septum is used. This is for illustration, and is not intended to be a detailed or physiologically accurate drawing.

FIGS. 1a to 1e show a nasal bridal applicator according to a first embodiment of the invention.

FIG. 1a shows an insertion guide with a stiffener, during insertion into the nose.

FIG. 1b shows the insertion guide of FIG. 1a with the stiffener removed and an introducer pushed along it, the introducer being prepared to enter the opposite nostril.

FIG. 1c shows the nasal bridle applicator, with the insertion guide in position and the introducer being pushed such that its end is directed through the opposite nostril.

FIG. 1d shows the bridle tape pulled through, and the insertion guide being removed.

FIG. 1e shows a nasogastric tube fitted, a bridle connector attached to the bridle tape, and the nasogastric tube attached to the bridle connector.

FIG. 2a shows an outer insertion guide.

FIG. 2b shows the outer insertion guide with an inner insertion guide core and an introducer fitted, in preparation for insertion into a nose.

FIG. 2c shows a transverse cross-section taken through the insertion guide, showing a passage formed between the outer insertion guide and the inner insertion guide core to guide the introducer.

FIGS. 3a to 3c show a method of use of the 2-part introducer of FIG. 2.

FIG. 3a shows the insertion guide having been inserted into a nostril, with the introducer ready to exit the guide and to be pushed into the opposite nostril.

FIG. 3b shows the introducer pushed through the guide, with the leading end protruding from the second nostril, ready to be pulled through.

FIG. 3c shows the insertion guide once the inner insertion guide core has been removed, and the introducer is being pulled through, with the bridle tape following.

FIGS. 4a and 4b show an embodiment of the invention that includes a thumbwheel to drive the introducer along the insertion guide.

FIG. 4a shows an isometric view of the drive-wheel on the 2-part insertion guide of FIGS. 2 and 3.

FIG. 4b shows a section of the drive wheel, with the internal core of the insertion guide in place, illustrating the arrangement by which it can drive the introducer along the guide passage.

FIG. 5a shows an insertion guide in a straight configuration fitted to a nostril.

FIG. 5b shows the insertion guide, within the nostril, activated to form a 'u-bend' in preparation for guiding an introducer.

FIGS. 6a and 6b show the insertion guide of FIG. 5 with a clip attachment, the clip facilitating a switch between the straight and bent configurations of the guide.

FIG. 6a shows the insertion guide and clip, the clip device set to maintain the leading end of the insertion guide in a straight alignment, in preparation for insertion or removal.

FIG. 6b shows the insertion guide and clip of FIG. 6a with the clip set in a second position, in which the leading edge of insertion guide is pulled to form a bent configuration, in preparation for introduction of the introducer.

FIG. 7a shows the introducer in the form of a spring surrounding a neck of a thread loop, a length of bridle tape being caught by the loop.

FIG. 7b shows the introducer after the loop has been pulled tight, firmly retaining the bridle tape. The leading end is covered with a ball.

FIG. 7c shows an alternative embodiment in which the introducer is in the form of a tube.

FIG. 7d shows another embodiment of the introducer in the form of a spring, with bridle tape pulled through it.

FIG. 7e shows a further alternative embodiment of introducer comprising a thin wire to which the bridle tape is attached at its leading end.

FIG. 7f shows a further alternative embodiment in which the introducer comprises a wire with smooth ball at its leading end and joined to the bridle tape at its trailing end.

FIG. 7g shows a preferred embodiment of introducer in which the embodiment of FIG. 7f is modified by fitting a spring over the thin wire.

FIG. 7h shows a modification of the FIG. 7g introducer in which a pair of thin wires are surrounded by the spring.

FIG. 7i illustrates a mechanism by which a ball end may be fitted to a wire core, as exhibited by various introducer embodiments of this invention.

FIG. 12a shows the bridle connector ready for attachment.

FIG. 12b shows the bridle connector with bridle-retaining part closed, as it would be when attached to bridle tape, and with tube-retaining part open, ready to receive a feeding tube.

FIG. 12c shows the bridle connector with all parts closed, as required to attach tube to bridle tape, the connector also showing a means of opening.

Figure 2C:
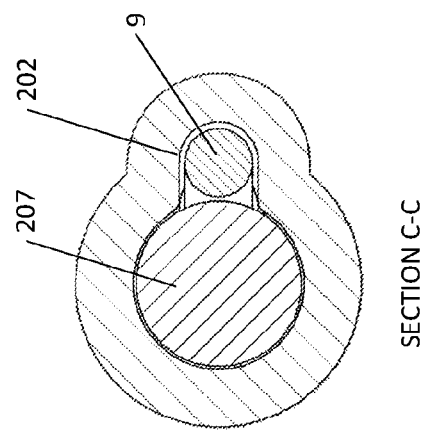
FIGS. 2a to 2c show a two-part insertion guide according to a second embodiment of the present invention.

With reference to FIGS. 1a to 1e, a method of fitting a nasal bridle using an insertion device in accordance with a first embodiment of the invention is described. FIG. 1e shows the ultimate aim of all embodiments of this invention. The nasal bridle 2 is fitted and retaining a feeding tube 12. Nasal bridle tape 10 is looped over the septum 3 and attached firmly to one part 110 of a clip 11. A second part 112 of the clip is attached to the feeding tube 12. One end 113 of the fitted tube leads into the stomach (not shown); a second end 112 is to be attached to a source of nutrients (not shown).

The fitting of the nasal bridle with the method and device of this invention is intended to be carried out with minimal trauma to the nose and septum.

Either nostril may be used to insert the bridle.

FIG. 1a shows an embodiment of the invention in which an insertion guide 7 has been inserted into a first nostril 5. The insertion guide 7 of FIG. 1a is made of a soft plastic or rubber. It has a pre-formed bend 102, which can be seen in its free state in FIG. 1b.

In order to make it easier to insert the insertion guide by reducing the effective diameter at the leading end 103, an insert 101, which is stiff relative to the tube, is inserted into the insertion guide before it is passed into the nose.

The insert is radiused at its leading end, to ease insertion. The insert has a mechanical stop 113 that abuts against a part of the insertion guide (a direction guide 13, in this embodiment) when it reaches the correct insertion depth. At this position, the radiused leading end of the insert protrudes a pre-determined amount from the leading end 103 of the insertion guide, such that the radiused end is just visible.

FIG. 1b shows the insertion guide positioned within the first nostril, and after the insert of FIG. 1a has been removed. Removal of the stiffer insert allows the flexible material of the insertion guide to relax and the end 113 of the tube resumes its natural U-shape. A direction guide 13 is fitted to the bottom of the insertion guide to assist a user in orienting the insertion guide 7 within the nostril 5 in order to ensure that the U-shape opens towards the second nasal passage. The guide 13 may take the form of a marking, and may be oriented in any direction, but advantageously it may be located (as shown) in the area opposite to the second nostril 6, so that it does not obstruct the clear nostril.

An introducer 9 has been fed into the insertion guide 7 until it reaches the exit of the U-shaped bend 102. At this point, further pushing on the guide 7 results in it being directed, from the bend exit, above the septum and into the opposite nostril. The introducer 9 needs to be sufficiently flexible to bend around the 'u-bend' 102, but rigid enough to be pushed along the insertion guide 7 and onwards through the opposite nostril 6. Ideally, this is achieved without the introducer 9 buckling and bunching up at the exit of the insertion guide and so preventing the leading tip being pushed out of the nose. Suitable examples of construction are: a thin wire, for example stainless steel wire or multi-strand steel cord; plastic tube, made from, for example, 60-90 shore A rubber or plastic; or a tightly wound spring, for example 0.15 wire, 1.3 mm outside diameter or similar. The introducer 9 is long enough to extend along the guide tube 7 and beyond the exit of the opposite nostril 6 with at least 2 cm protruding from both nostrils (see FIG. 1c).

In some embodiments, the introducer 9 may have a ball or similarly shaped piece on the end to present a smooth edge to the nostril interior.

In other embodiments, the introducer 9 may have a bend a short distance from the tip. This can help the tip of the introducer avoid sticking on any obstacles, e.g. anatomical 'steps' in the nostril, by rotating the introducer while pushing, the bend allowing the tip to move over the edge of any obstacle.

The introducer may be pre-lubricated with a water-activated lubricant (and wetted before insertion to activate the lubricant), or alternatively water-based lubricant (e.g. K-Y gel) or any other lubricant that is compatible with nasal tissues could be applied before insertion. Lubricant can make a very significant difference to whether or not the tip of the introducer will pass through a tight nasal passage.

Bridle tape 10 is attached to the introducer 9. The join 114 may be made by any appropriate one of the common joining methods that are already well known in the art: adhesive, shrink-wrap, sewing, or crimping the end of the introducer to retain the inserted end of the bridle tape, among other examples. The choice of method should maintain secure fastening whilst presenting a low profile and smooth edges. These latter features minimise the diameter of insertion guide needed, and help prevent obstruction when the introducer is being pulled through. Alternative constructions are shown in FIG. 7.

FIG. 1d shows the bridle tape 10 after it has been threaded through both nostrils 5, 6. The insertion guide 7 has been removed, leaving a free cut end 109 of the bridle tape, and the bridle tape is threaded through the nose. The free cut end 109 of the bridle tape 10 is then held to prevent it pulling out of the nostril while the insertion guide 7 is removed. As the guide 7 is pulled downwards, the bend at the leading end (now trailing end) of the insertion guide 108 is flexed and straightens out to fit inside the nostril. Removal of the insertion guide leaves the loop of bridle tape 10 threaded about the septum, with each end protruding from a respective nostril. The tape 10 is ready for the attachment of a bridle connector.

Figure 2B:
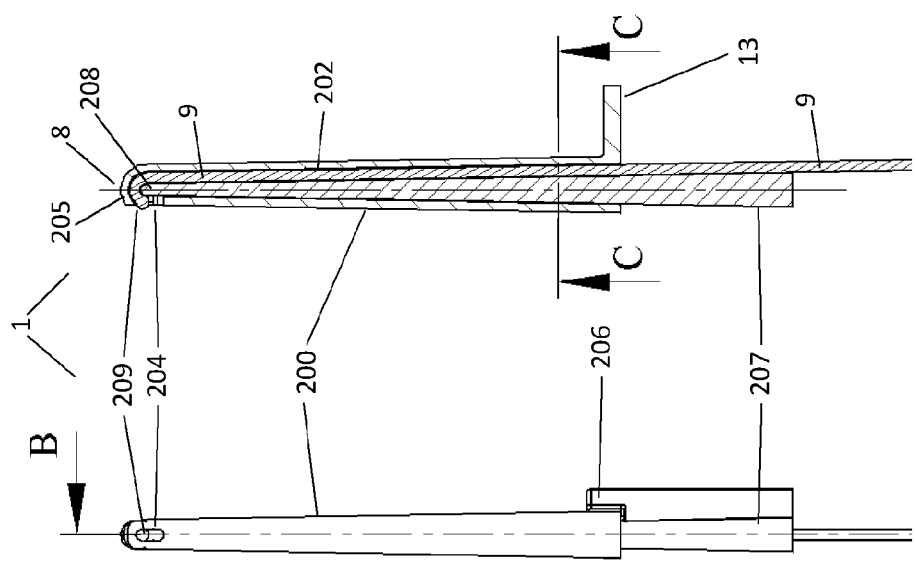
Figure 2A:
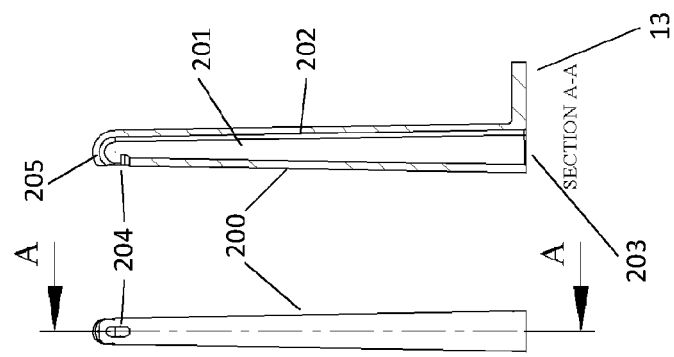

An alternative design of insertion guide for use with this invention is shown in FIGS. 2a-2c.

FIG. 2a shows an outer insertion guide 200, consisting of a substantially tubular passage 201, open at one end 203 to receive an inner insertion guide core (shown in later drawings). Opposite the open end, there is a closed end 205, of spherical form internally. An opening in the side near the top 204 is located near the closed end. An adjacent passage 202 is located alongside the main passage 201, its shape most clearly shown in FIG. 2c. The adjacent passage 202 also extends from the open end 203 to the opening 204, follows the outside of the spherical part of the closed end 203, and is substantially the same cross-section throughout.

The outer insertion guide 200 can be made by any one of the standard manufacturing methods known in the art, but most advantageously would be by plastic moulding. In the embodiment shown in FIG. 2, the closed end 205 is smaller in diameter than the open end 203. This taper is to assist the removal of the part from a core that forms the internal shape of the guide 200 during the moulding process.

The outer insertion guide 200 has a direction guide feature 13 to assist the user in orienting the opening 204 such that, when fully inserted in a nostril, it is directed over the septum towards the second nostril.

FIG. 2b shows an outer insertion guide 200, an inner insertion guide core 207 and an introducer 9 assembled in preparation for insertion into a nose. The tip of the introducer 209, located within in the opening 204, is rounded to promote smooth travel and to reduce the risk of the introducer digging into soft tissue. The insertion guide inner core 207 is inserted into the insertion guide external core, such that the tip 208 of the inner insertion guide core closely fits the spherical end 205 of the outer insertion guide. The adjacent passage 202 is left open. With this arrangement, a 'u-bend' 8 is defined above the tip 208 of the inner core 207 between the adjacent passage 202 and the opening 204. The introducer 9 is inserted into the adjacent passage 202, in which it forms a close, but clearance fit. The 'u-bend' 8 formed within this construction serves to guide the introducer through an angle between 135° and 170° relative to the axis of the insertion guide. In this way, if the insertion guide is fully inserted along one nostril, the introducer will be guided towards the other nostril. The precise angle is determined by the location of the opening 204 relative to the end of the adjacent passage 203.

In one embodiment, the insertion guide inner core 207 has a clip feature 206 that hooks over the direction guide 13 such that the insertion guide inner core is maintained in the correct position within the outer core during use. The clip feature is engaged by rotating the insertion guide inner core, once fully inserted. Such clip features are well known to one skilled in the art, can take many forms, and do not need to be explained in depth. This clip can be seen more clearly in FIG. 4a, where the clip 406 on the inner insertion guide core 407 is retained over a ledge 409.

The guide 200, 209 may be used in combination with most of the embodiments of introducer 9 described herein, with one additional consideration. In this embodiment, the u-bend 8 is tighter than that featured in the embodiment shown in FIG. 1 and so more force is required to push the inserter along the adjacent passage. As a consequence, it is found that an inserter in the form of a tightly-wound spring is particularly advantageous. A spring with 1.3 mm outside diameter coiled from 0.15 mm wire has been found to work, but springs with other dimensions may also be used.

FIG. 2c shows a section of the insertion guide, in which the profile of the adjacent passage 202, formed between the outer insertion guide and the inner insertion guide core 207, is illustrated. As stated previously, the adjacent passage is to guide the introducer 9 and its cross-section is substantially the same all the way along.

To minimise discomfort as it is inserted into a nostril, it is advantageous for the insertion guide to be as small as possible in cross-section. One advantage of the insertion guide of FIG. 2 is that the full 'u-bend' is formed within the diameter of the insertion guide, and the need for a bend to go over the top of the septum is obviated.

After insertion of the assembled insertion guide 200, 209 and introducer 9 into the nostril, the method of threading the nasal bridle proceeds as illustrated in FIGS. 3a to 3c. Thereafter, the method of securing the bridle and attaching the feeding tube proceeds as described in relation to the embodiment depicted in FIG. 1.

FIG. 3a shows the insertion guide of FIG. 2b fully inserted within a first nostril 5, such that the opening 304 is above the top of the septum 4. FIG. 3b shows the introducer pushed through with the leading end protruding from the second nostril, ready to be pulled through. The u-bend 8 is a continuation of the adjacent passage between the outer insertion guide and the inner insertion guide core. Before the introducer 9 is pulled fully to draw the bridle tape 10 through, the inner insertion guide core 307 is removed. FIG. 3c shows the situation after the core is removed and the introducer is being pulled through, with the bridle tape 10 following. The bridle tape is around 30 cm long, although shown shorter here for diagrammatic reasons. The opening 304 above the top of the septum provides support while the introducer and tape is pulled through, minimising the risk of trauma to the back of the septum 4

FIG. 4 show an exemplary thumbwheel that may be used to drive the introducer along the insertion guide in various embodiments of this invention. The use of a thumbwheel to assist with this procedure makes it possible for the u-bend at the top of the insertion guide formed by the adjacent passage to be tighter. This in turn allows the top of the insertion guide to be made smaller in size. The thumbwheel allows the introducer to be pushed more conveniently and with more force, without collapsing, compared to pushing with fingers.

FIG. 4a shows an isometric view of the drive-wheel on the 2 part insertion guide of FIGS. 2 and 3. FIG. 4b shows a section of the drive wheel, with the internal core of the insertion guide in place, showing how it can be used to drive the introducer along the guide passage. The description will refer to both of these figures interchangeably.

Location for an axle 403 is formed by a pair of arms 402 protruding from the outer insertion guide, 400. The arms have a hole through which an axle can be inserted and retained by any of a number of known methods. A drivewheel 411 fits on the axle. The diameter of the drive wheel 411 and the position of the hole for the axle 402 are arranged such that the driving features 412 on the drive wheel 411 are engaged with the introducer 9 when the inner insertion guide core 407 is fitted. Advantageously the inner insertion guide core is made of a low friction plastic, for example: Acetal, PTFE, nylon or a plastic with a low friction additive such as molybdenum disulphide or PTFE. Such materials are well known in the art. Alternatively the inner insertion guide core may contain a small pad of a low friction material locally to the same effect. The surface 413 may, additionally or alternatively, be lubricated with any suitable lubricant. This means that the surface of the inner insertion guide 413, opposite to the contact of the drive wheel 411 is designed to offer minimal resistance to movement of the introducer 9 when it is driven by the drive wheel.

The drive wheel 411 has engaging means 412 on its periphery, such that rotation of the drive wheel 411 causes the introducer 9 to be driven in the direction of movement of the side of the drive wheel that is in contact with it. The engaging means 412 may consist of a high friction material in compression, such as a rubber or polyurethane, or teeth 415 which engage with the introducer.

The surface of the drive wheel on the region 414 is moved by a user's fingers to rotate the wheel. This causes the advancement of the introducer through the insertion guide.

FIG. 5 show a further embodiment of a nasal bridle applicator in accordance with this invention. This embodiment is particularly advantageous to a number of applications. First, the U-bend is easy to straighten, which makes for more comfortable insertion and removal. Secondly, the applicator can bend around the posterior of the septum, to protect it fully while the introducer and bridle tape are being threaded through. Thirdly, this insertion guide has a large u-bend in comparison to the embodiments shown in FIGS. 2 and 4, which dispenses with the requirement for a drive means according to FIG. 4. The u-bend of this embodiment can readily be straightened in situ, even whilst supporting the threaded bridle tape. This allows for comfortable removal and, as the bend is straightened other than by the force of the septum, reduces the need for the insertion guide to be fabricated from material as soft as that required for the insertion guide of FIG. 1.

Figure 5B:
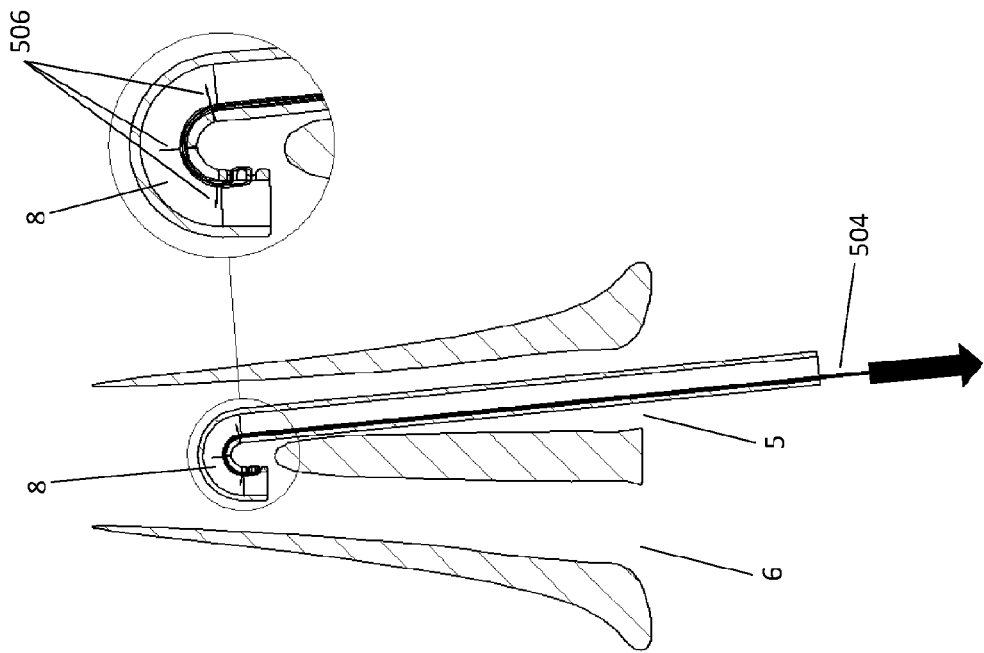
FIGS. 5a and 5b show a further embodiment of the nasal bridle applicator of the present invention.
Figure 5A:
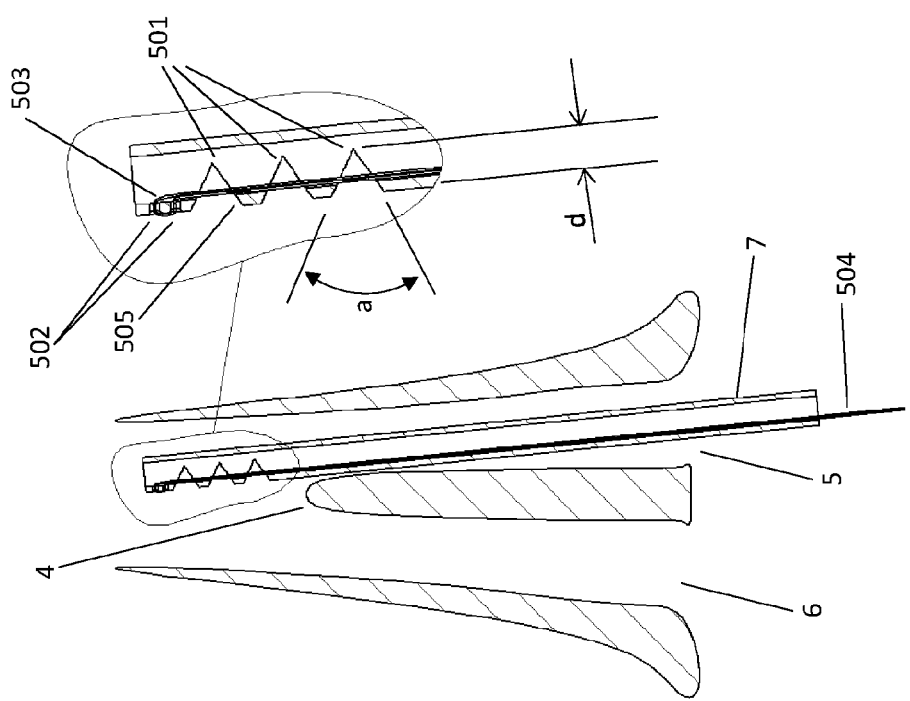

FIG. 5a shows an insertion guide 7 in a straight state fully inserted into a nostril. The insertion guide can take the form of an extruded tube, in a soft material such as rubber, thermoplastic elastomer (TPE), polyurethane, or other suitable material. The leading end of the insertion guide has a number of v-slits 501 (see inset) along one side, whose purpose shall become clear. An actuating lead consisting of thread or wire or cord 503 is attached to the insertion guide by being threaded through two holes 502 and the two ends threaded down to the bottom of the insertion guide, where the free ends 504 protrude. The attachment of the actuating lead does not have to be as shown, but can be by any common attachment mechanism to the region of the insertion guide above the v-slits and on the side of the widest point of the v-slits. For example, instead of threading through the two holes 502, the actuating lead could thread through the top of the insertion guide, and be inserted into the topmost of the v-slits. The actuation lead could be knotted at the top of the insertion guide, so only one end 503 protrudes from the bottom of the insertion guide.

The whole insertion guide could be fabricated in any of a number of known ways. For example, it may be cut from one piece of tube, moulded as a single tube, or the end with the v-slits may be insert moulded directly to a piece of tube or moulded separately and then attached to the end of a tube.

The external edges of the insertion guide and of the v-slits are advantageously radiused so that there are no sharp edges to catch or damage the soft tissues inside the nose. For an insert moulded part, the radii can be in the form of the tool. For a part cut from a tube, the radii can be formed by the brief application of high heat, which preferentially melts and smoothes sharp edges.

FIG. 5b shows an insertion guide, inserted into one nostril 5, activated to form a u-bend 8 ready to guide an introducer down the opposite nostril 6. When the actuating lead is pulled, the v-slits 501 close up, to form a u-bend 8, that can guide the introducer as previously before. The angle, a, along with the number and spacing of the v-slits can be adapted to make the radius of the u-bend and the angle through which it rotates larger or smaller. The dimension d, the depth of the v-grooves relative to the tube diameter, can be adjusted to make the tube bend with less force. If the depth d, of the v-slits is varied across the array of slits, the v-slits can be made to bend in the order of the depth, deepest first. Use of different depth v-slits can make the bend form in a tighter space. If the top v-slit is deeper, it will bend first, and so this section of insertion guide would already be bent by the time the bend at the second v-slit commences. With these guiding principles, it is a straightforward to come up with dimensions that will work as an introducer in a nasal bridle insertion device. Preliminary work indicates that effective results are achieved with an embodiment with five v-slits subtending an angle, a, of 60° and with a depth d of about 60-70% of the tube diameter, with 3.5 mm outside diameter and 2.6 mm inside diameter tube in 70 shore polyurethane. It is though anticipated that other combinations of dimensions and materials will also be effective. Alternative materials include, for example, rubbers, TPE, soft plastics such as LDPE and others.

Advantageously, the tube diameter for the insertion guide is chosen to be as small as possible, to enable the guide to pass easily up smaller nostrils, although it must also have an inside diameter sufficiently large to pass the introducer and bridle tape without significant resistance. How best to strike a balance between these requirements will be apparent to one skilled in the art.

FIG. 6 show the insertion guide of FIG. 5 with the addition of a two-position clip device. The clip device enables the insertion guide to be held in either a straight state, or a state with a u-bend, the latter enabling the introducer to be inserted, while the 'u-bend' is maintained. The clip housing may also act as a direction guide 13 to assist the user in determining the orientation of the u-bend.

FIG. 6a shows an insertion guide with a clip device, the device being shown in a position to keep the actuating lead slack so the leading end of the insertion guide is free to be straight, as would be needed for insertion or removal. Details of the clip mechanism are shown and described but it will be apparent to one skilled in that are that there are many constructions and variations, of which this is just a single example, that could equally be used to perform the same function.

The clip device consists of three parts—a clip body 602, a clip 605 and a clip cover 604, which holds the clip inside the body. In the embodiment shown, the cover is held to the clip body with four screws 613, but the screws can clearly be replaced with any common joining method, such as adhesive, ultrasonic welding, clipping together etc.

The insertion guide 7 is fixed into the clip body 602 by any of the common methods—interference fit, adhesive, melting together etc. As part of this, the insertion guide may be pushed down to a stop 615, to control the depth of insertion.

The device includes a passage 612, which is substantially in line with the axis of the insertion guide, and of a diameter similar to the inside diameter of the insertion guide. The passage is open to the insertion guide at its top and to the outside at its bottom. The passage 612 provides means for an introducer, as described earlier, to pass through the clip body 602 into the insertion guide.

The actuation lead 603 passes from the bottom of the insertion guide and is fixed firmly in the clip 611 by adhesive, a tapered pin, a knot, or any other suitable method of fixing.

The clip 605 is moveable between the two positions shown in FIGS. 6a and 6b. The clip has two protruding arms 606 extending through slots 607 in the cover and the clip body 602. The slot in the clip body and the arm protruding though it is not seen, but these are the same as the slot in the clip cover. The arms 606 can be used to move the clip from the first position to the second position, where a lug 609 on a resiliently flexible arm engages with a slot 610. The travel between the two positions is designed to be sufficient to tighten the actuation lead 603 from a position where it is slack and the insertion guide is straight, with the v-slits 601 open, to a position where the actuation lead is tightened, closing up the v-slits 601 and forming a u-bend 8.

The flexible arm 614 of the insertion guide extends beyond the clip body. Pressing down in this region, disengages the lug 609 from the slot 610, allowing the clip to return to the first state, and allowing the tension on the actuation lead to be released, and the insertion guide 7 to return to the straight state of FIG. 6b.

The clip can be activated from either side to enable use in either nostril.

FIGS. 7a to 7i show details of embodiments of the introducer, including its connection to the bridle tape. In these figures the middle section of the introducer is not shown in order to illustrate more conveniently the features at the ends.

Figure 7C:
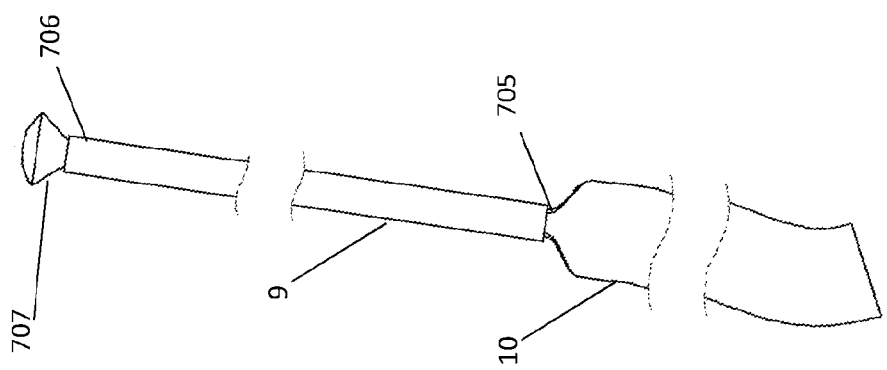
FIGS. 7a to 7i show various embodiments of the introducer of this invention and its connection to the bridle tape.
Figure 7B:
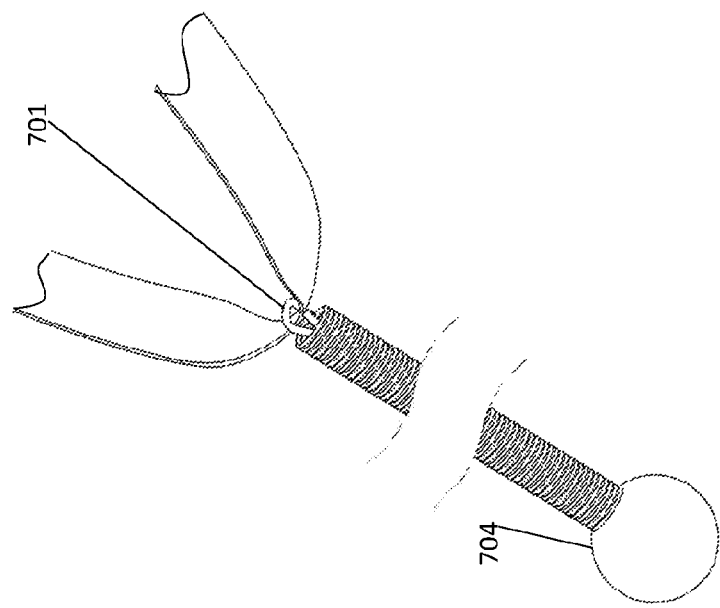
Figure 7A:
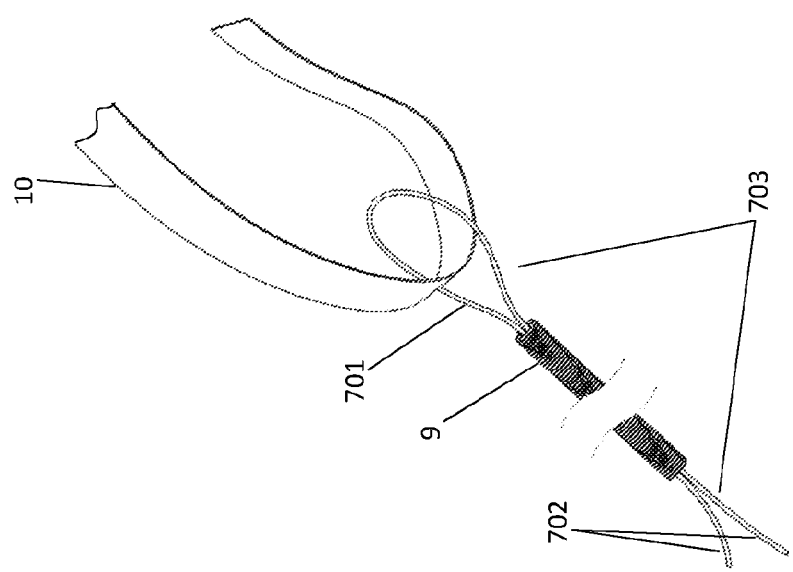

FIG. 7a shows the introducer 9 in the form of a spring, with attachment means 703 consisting of thread, wire or other cord extending longitudinally through it to form a loop 701 extending from one end with free ends 702 trailing from the other. A length of bridle tape 10 is pushed through the loop, before the thread is tightened and fastened.

FIG. 7b shows the introducer 9 ready for use, where the free ends of FIG. 7a have been pulled tight and knotted or retained at the leading end of the introducer, by which means the loop at the trailing end of the introducer 703 has been pulled tight, firmly retaining the bridle tape. The leading end has been covered with a ball 704. Although a ball is shown other shapes may be advantageous, for example the shape could be one sided, to complement the effect obtained from a bent introducer, of the type shown in FIG. 10.

In some embodiments, the ball 704 is brightly coloured. In others, it includes a light. These features assist in providing a contrast with the nose and to make the introducer more easily visible to a user as it is pushed towards the nostril exit.

In embodiments in which the introducer is in the form of a spring, the attachment means 703 inside it may advantageously prevent uncoiling.

The level of tension of the attachment means 703 between the ball 704 and the loop 703 may be varied to affect the stiffness of the spring: a tighter loop makes it stiffer.

Additionally the introducer could have a wire or other long, thin material inserted along all or part of its length, to alter the stiffness in bending of one, or other of all, or part of the length of the introducer. For example it may be an advantage for the introducer to be a little less stiff at the leading edge, allowing the ball to find its own way past obstacles, and more stiff in the remainder, preventing the introducer from buckling in such a way that it cannot be pushed through a tighter nostril.

As will be obvious to one skilled in the art, and as described above, other constructions of introducer that are capable of performing the same function are possible. For example, the spring could be replaced with a tube; the bridle tape could be threaded through the whole introducer; the introducer could be formed by applying stiffening means such as adhesive to a part of the length of the bridle tape.

FIG. 7c shows an embodiment of the introducer in which it is in the form a tube 9. The bridle tape is threaded from the back of the introducer 705 to the leading end 706. The end of the bridle tape 707 is protruding from the end of the tube, where it can be captured by adhesive, or over-moulded with a ball or other smooth shape to retain it and provide a leading part that will not catch.

Figure 7F:
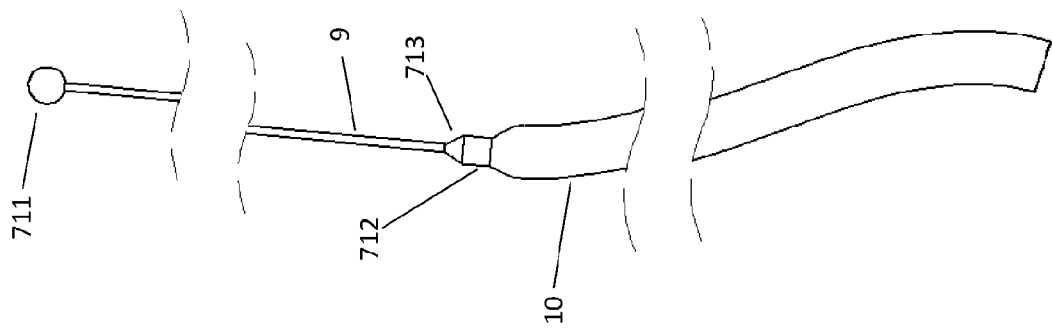
Figure 7E:
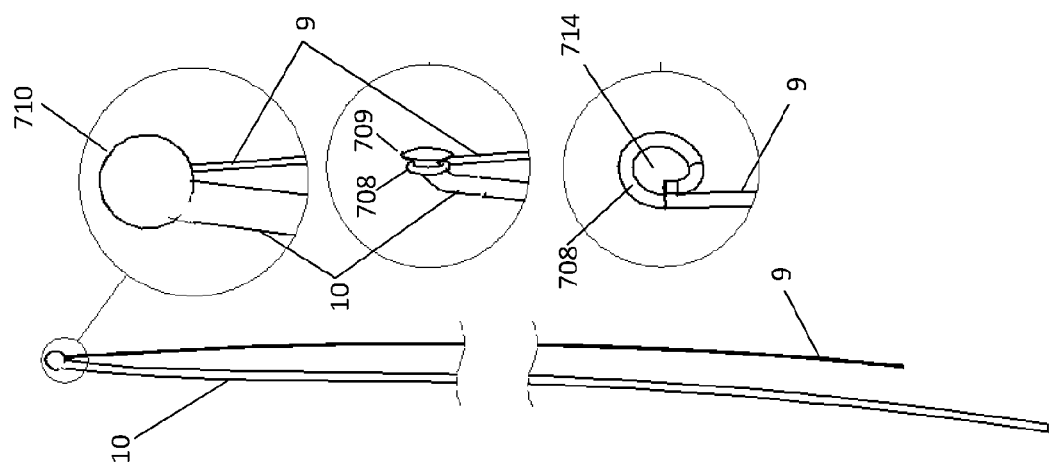
Figure 7D:
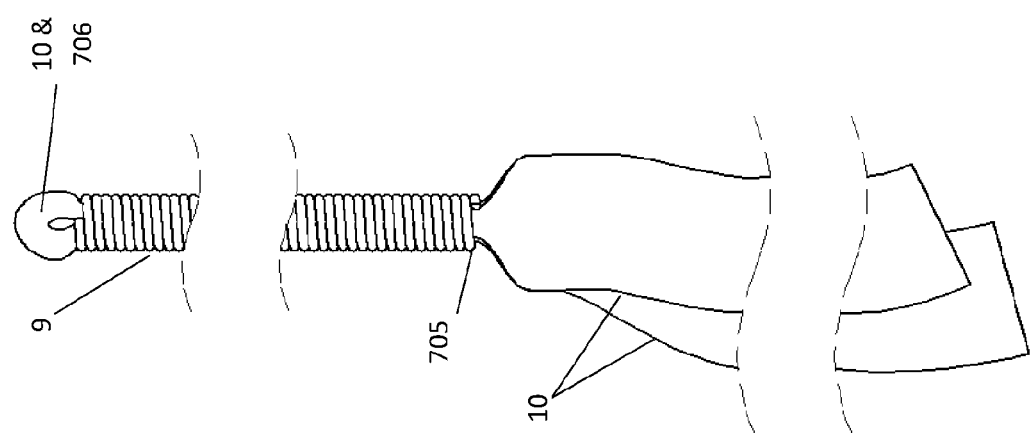

FIG. 7d shows an embodiment of the introducer in which it is in the form of a spring. A loop of thinner bridle tape 10 has been pulled through, leaving a small loop protruding at the leading end 706, and free ends protruding from the trailing end 705. In this arrangement, the nasal bridle consists of two loops of bridle tape.

FIG. 7e shows a still further design of introducer in which the diameter of material having to pass through the insertion guide is minimised. In this embodiment, the bridle tape 10 is attached at its leading end to a wire of metal or plastic 9 and over-moulded with a smooth shape, for reasons already described. The small detail views of FIG. 7e illustrate a possible method of fabrication. A small loop 708 is formed in the leading end of the introducer wire. The bridle tape is pushed into the open gap in the loop 714, the bridle tape and loop being such that the tape is held tightly, and can be cut off 709. The loop plus bridle tape combination then has a smooth shape over-moulded to cover the end and to bond the parts together. Alternatively, instead of the loop shown, the wire may be knotted tightly around the bridle tape before cutting off the excess wire and bridle tape prior to over-moulding FIG. 7f shows a further design of introducer. A wire of metal or plastic 9 is attached to the bridle tape 10 by a tight u-shape (not shown) in the wire hooking into an end of the bridle tape. The two are inserted into a mould tool, the bridle tape compressed tightly around the wire. A join 712 is over-moulded to hold the parts together. The join has a tapered leading edge 713 to aid smooth passage through the insertion guide and nose.

An alternative and advantageous join may be formed by an alternative method that again begins by hooking a tight u-shape in the wire to the bridle tape 10. The short end of the bridle tape is cut and a small amount of adhesive, for example epoxy, or a UV-curing adhesive, is applied to the 2 or 3 mm towards the end of the tape. The tape is then pulled into a tight-fitting hole in a non-stick plastic such as PTFE or Acetal. As it is pulled in, the loop of wire is tucked into the tape. The adhesive is then set within the hole. This creates a chemical bond to the wire and to the tape, but also a mechanical bond around the fibres of the tape and the loop of the wire, making the bond very strong. The join in this instance also exhibits a low profile, making it extremely attractive for this nasal application.

Alternatively, once the wire is hooked into the tape, ultrasonic welding may be used to melt the tape material around the wire, without the use of adhesive. In this embodiment, the tape plus hooked wire is again pulled into a tight-fitting hole in a non-stick plastic, although this time without adhesive. The plastic in this embodiment also includes a slot extending radially from the hole and positioned a short length (1-3 mm) from the end of the hole from which the bridle tape protrudes. A sonotrode is used to weld the join and the base of its is shaped to reform the original rounded shape of the hole, when fitted within the slot. To weld the join, the sonotrode blade is located in the slot with the tape and wire loop positioned underneath it. Activation of the ultrasonic welder causes the tape to melt around the wire loop and form a strong bond. The complementary shape of the hole and the blade mean that the resulting join is round and of very low profile.

As in previous designs, a ball 711 is over-moulded on the leading end of the wire.

Figure 7I:
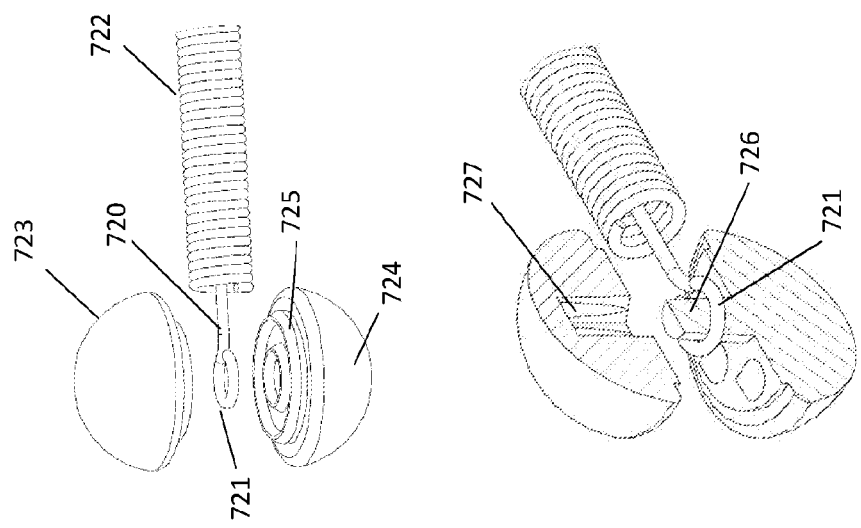
Figure 7H:
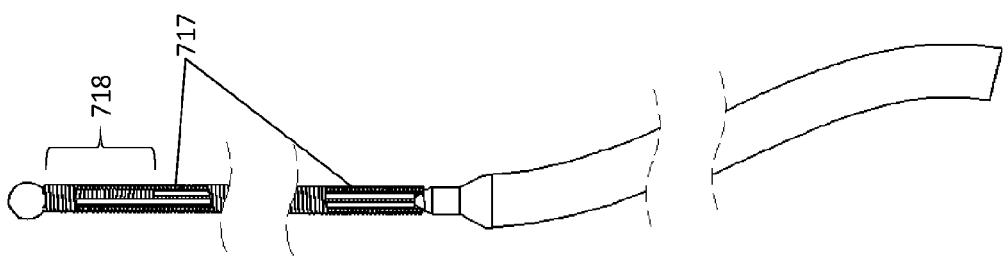
Figure 7G:
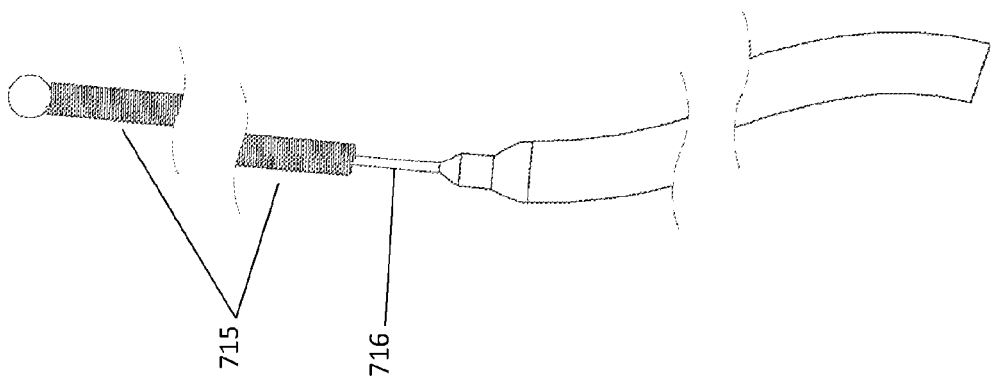

FIG. 7g shows a slightly modified version of the introducer embodiment shown in FIG. 7f. A spring or tube 715 is fitted over the wire 716, sufficiently loosely to allow easy rotation of the wire within. The spring is also permitted some degree of movement along the length of the wire. This enables the wire 716 to be pushed to be ahead of the outer spring or to be located wholly within it. The former arrangement provides a more flexible part at the leading end of the introducer; the latter provides a stiffer leading end, having the stiffness of the outer spring plus the stiffness of the inner wire. This capability allows inducer performance to be tailored according to the needs of the insertion.

FIG. 7h shows a further modified version of the embodiment of introducer shown in FIG. 7g. This embodiment includes a second inner wire 717 attached to the bridle tape at one end and extending the majority of the length of the outer spring towards, but falling short of, the leading end of the introducer. A section 718 towards the leading end is therefore more flexible than the remainder of the introducer, with two inner wires. This section 718 can therefore more easily bend to find its way around any obstacles. The remainder of the introducer however is relatively stiffer, assisting in pushing through a nasal passage.

FIG. 7i shows two exemplary ways by which a ball end, as shown in the introducer embodiments of FIGS. 7b, 7f, 7g and 7h may be fitted to the end of the introducer. An inner wire 720 of the introducer is formed into a small loop structure 721 at its leading end. The introducer shown has a coiled spring 722 surrounding the wire 720, although other embodiments are equally amenable to this process. Upper 723 and lower 724 hemispherical structures are fitted about the loop 721 and ultrasonically welded or otherwise bonded. The loop of the wire captured in the bond gives a strong mechanical bond. Advantageously, complementary ridges 725 are formed on the adjoining surfaces of the hemispheres to improve stability in the resulting structure. Advantageously, one hemisphere includes a tapered peg 726 extending from its flat surface. The other hemisphere includes a corresponding hole 727. The fit between peg 726 and hole 727 is such that the parts grip when pushed together. In assembling the ball, the peg 726 is first passed through the loop 721 formed at the end of the wire 720. The two hemispheres are pressed together, the hole 727 fitting over the peg 726 and trapping the loop 721. In one embodiment, the parts are then placed under an ultrasonic welding machine and the two hemispheres permanently welded together. In an alternative embodiment, adhesive may be applied to the adjoining surfaces, for example to the hole 727, before bringing the two parts of the ball together. In either case, the result is a strongly-bonded spherical structure affixed to the leading end of the introducer, which is advantageous in pushing through a nasal passage.

Figure 8:
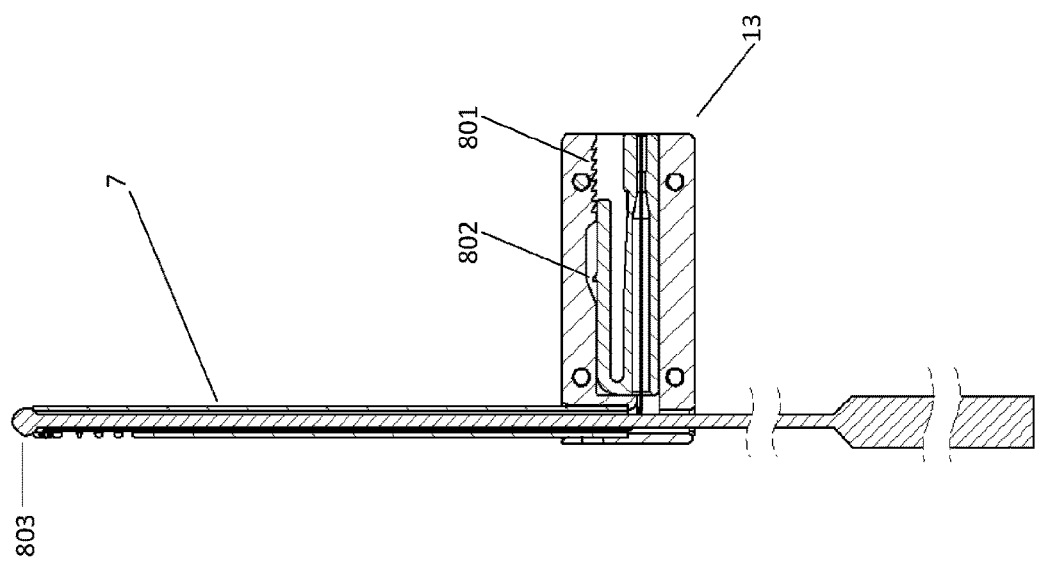
FIG. 8 shows an alternative example of a clip attachment to that shown in FIG. 6, for use with this invention.

FIG. 8 shows an embodiment of the nasal bridle insertion device according to the present invention, ready for use. The insertion guide 7 is in its straight configuration. The introducer 9, with a smooth shape 803 on the end, is inserted in the guide 7 and any required lubricant has been applied.

Lubricant may be applied to the insertion guide, introducer, or the nostril. Any suitable lubricant can be used, or it may be advantageous for the insertion guide and introducer to be pre-coated with a water-activated lubricant and wetted before insertion.

In using the device, the clip is first set to put the guide in its straight configuration, as shown in FIG. 6a, or FIG. 8, with the actuation lead slack. The leading end of the insertion guide 7 is therefore straight and, in this position, is passed into the first nostril, until the end section, with the v-slits, is clearly above the septum. The rounded end of the introducer 803 facilitates smooth insertion into the nostril. The clip also performs a function of a direction guide 13 as previously described. With the guide in position, the clip is moved to its second position to pull the actuating lead and to force the leading end of the insertion guide into a u-bend configuration. Next, the insertion guide is lowered gently, within the first nostril, until some resistance is felt, indicating that the u-bend is positioned around the posterior septum.

The introducer is then pushed through. In most situations, there is likely to be reasonable force feedback, which enables action to be taken to move the introducer past any obstacles, such as an anatomical step in the opposite nostril. If such an obstacle is hit, the introducer may be rotated such that a bend close to the end of the introducer assists in moving the tip over the edge of the obstacle. Alternatively, movement of the introducer could be reversed, the introducer rotated and then pushed again, such that the tip takes a different path to avoid the obstacle. The last emergence from the nose may require hooking out, with a tool or tweezers, as the ball can get stuck on the overhang of the nostril.

Once the tip of the introducer emerges from the opposite nostril, it is pulled through until about 50 mm of bridle tape protrudes from this nostril.

Throughout this procedure, the u-bend of the insertion guide protects the top of the septum, preventing both the introducer and bridle tape rubbing it.

Finally, the clip is then returned to its first position, as shown in FIG. 6a, and so the insertion guide is again straight. The free end of the bridle tape is held, and the insertion guide removed from the first nostril.

After this insertion procedure, the ends of the bridle tape protrude from respective nostrils. The two ends are held together and a bridle connector attached, close to the bottom of the nose. At this point, excess bridle tape, together with the introducer, are cut off and discarded. The feeding tube is then inserted and attached to the bridle connector.

Alternatively, the feeding tube may be fitted before the bridle connector is attached and connected.

The clip shown with the nasal insertion device of FIG. 8 differs from the embodiment shown in FIG. 6a. In this alternative embodiment, the clip is stoppable in multiple positions, enabling the tension in the actuation lead to be set to various discrete levels. This, in turn, allows the angle of the 'u-bend' to be adjusted, for more accurate guiding of the introducer into the opposite nostril. This is achieved by a clip construction in which the single stop 610 and lug 609 of FIG. 6 is replaced by multiple saw-tooth shaped slots 801 and a correspondingly shaped mating protrusion 802 that can be located in any one of the slots 801.

If the clip is pulled further away from the slack, straight position seen in FIGS. 6a and 8, the bend will become tighter and the angle between the leading end and a longitudinal axis of the insertion guide increases. This mechanism may be used to accommodate different septum sizes.

Figure 9:
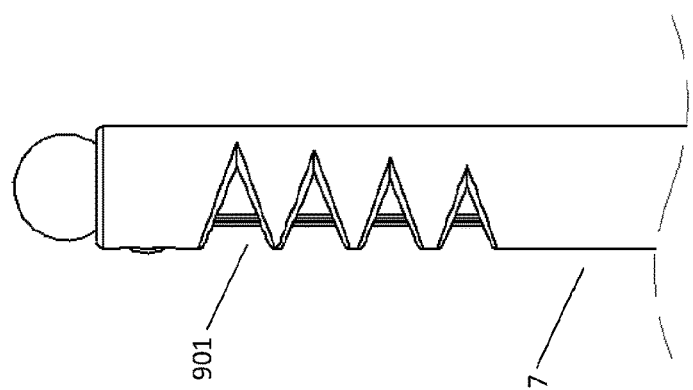
FIG. 9 illustrates an alternative version of the embodiment shown in FIG. 6, with an insertion guide of varying slit design and in which an introducer with ball tip is fitted, the ball tip providing a smooth end to assist passage along a nostril.

FIG. 9 shows an alternative arrangement of the v-slits at the top of the insertion guide of FIG. 6a. In this embodiment, there are more slits formed at a shallower angle, and the topmost slits are deeper than the lower ones. This results in the bending being initiated at the uppermost v-slit.

Figure 10:
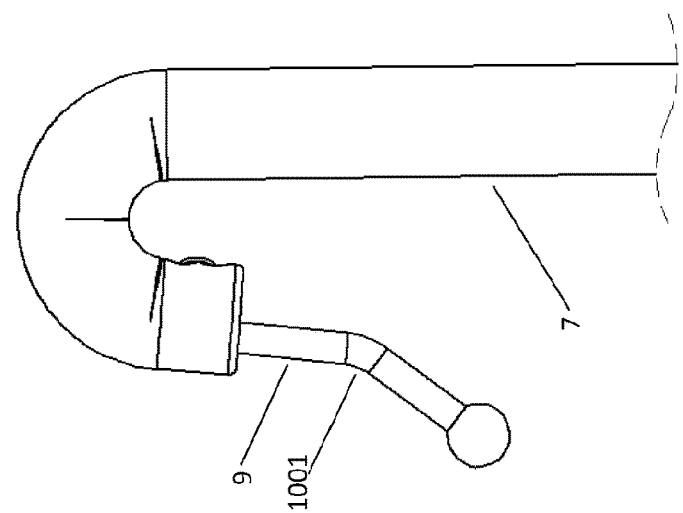
FIG. 10 shows an insertion guide according to FIG. 5b fitted with an alternative design of introducer, with a bend at its leading end.

FIG. 10 shows an insertion guide 7 of the type shown in FIG. 5b. This guide 7 is used with an introducer 9 similar to the type shown in FIG. 7b, but with a bend 1001 built in to the introducer, close to the leading end. The purpose of this bend is to assist the introducer in clearing any obstacles that may arise in its exit passage through the second nostril. If such an obstacle is encountered, the introducer may be withdrawn slightly, rotated and moved forward again, in the hope that the re-oriented leading edge then steers past the obstacle.

Figure 11:
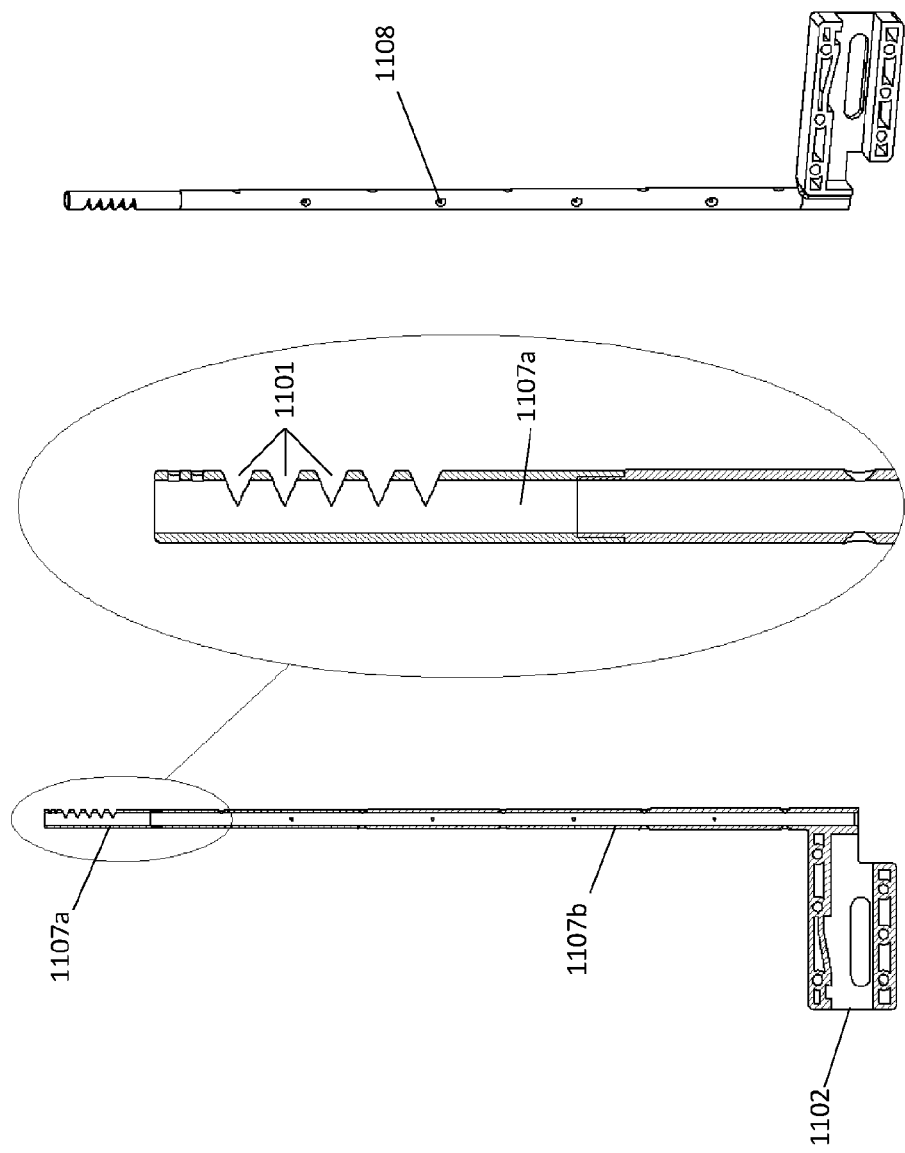
FIG. 11 shows an alternative embodiment of insertion guide with clip attachment, in accordance with the present invention.

FIG. 11 shows an alternative construction of the insertion guide shown in FIGS. 6a and 8. That is, the type with a clip to control bending of the guide tip via an array of v-slits. This embodiment has advantages in both manufacturing and use. In this embodiment, the insertion guide 1107 has two distinct parts: an upper lead end 1107a and a lower guide shaft 1107b. The upper lead end 1107a includes the v-slits 1101 and forms the u-bend. The lower guide shaft 1107b comprises the major part of the guide 1107 and is formed as an integral part with the body 1102 of the clip.

The requirement for a flexible part to form the u-bend places clear constraints on the material that may be used to fabricate the guide 1107. The more obvious options include TPE (thermoplastic elastomers) or TPU (thermoplastic polyurethane) materials. These materials are however difficult to mould. In particular, they have a relatively low melt flow index, which renders it practically impossible to fill the length of a guide tube mould, whilst keeping the wall thickness and therefore outside diameter as small as possible. It is however desirable to be able to mould the device as this allows the shape of the part to be readily controlled, making the required smooth edges easy to achieve. By limiting the need for this flexible material to only the upper lead end 1107*a* of the guide tube, manufacturing requirements are far less stringent. The relatively short length of this section 1107*a* means that the TPE or TPU materials can readily be moulded for the length of this portion to provide the flexible tip.

The lower guide shaft 1107*b* does not have to form the flexible tip and so its material requirements are less stringent. In the embodiment shown, it is formed of the same material and integrally with the body 1102 of the clip. Typically, this part 1102, 1107*b* is fabricated from a soft polypropylene, polyethylene or similar plastic that is a little harder and stiffer than the tip portion. Plastics of this type that have a very high melt flow index are readily available and so can fill the length of a mould for the tubular part of the insertion guide comfortably. During the moulding process, the guide core is formed by moulding around a centrally-located tubular part within the mould tool. The part is held in place by supporting pins that extend radially through the mould tool. Their use in the moulding process is evidenced by a series of holes 1108 that are apparent in the mould-produced lower guide shaft.

The upper lead end 1107*a* with the v-slits is formed by over-moulding the flexible material onto the main body 1102, 1107*b*. The particular materials selected for these parts will be chosen so as to form a strong bond during over-moulding.

The advantage in use of this construction is that when the bent configuration is adopted, bending is more concentrated in the more flexible and less stiff leading end 1107*a*. If the insertion guide shaft 1107*b* is formed of the same, softer material as the leading end 1107*a*, then bending tends to occur along the entire length of the shaft. This makes it more difficult to manipulate the insertion device in use.

In the embodiment shown, the integral construction of the insertion guide shaft 1107*b* and clip body 1102 allow them to be fabricated in materials that are amenable to a moulding process. It is, of course, not necessary to have them integrally constructed and the advantages of this embodiment can alternatively be achieved by moulding the parts separately, but using materials with the required moulding and performance characteristics.

FIG. 12 show an example of a bridle connector for use with embodiments of the present invention. The connector has one part to attach to the ends of the bridle tape after it has been threaded through the nose, and a separate part to attach a feeding tube. The connector also includes a means to detach from the tube and re-attach to another tube. This has the advantage that the feeding tube can be changed without the need to replace the nasal bridle.

Figure 12C:
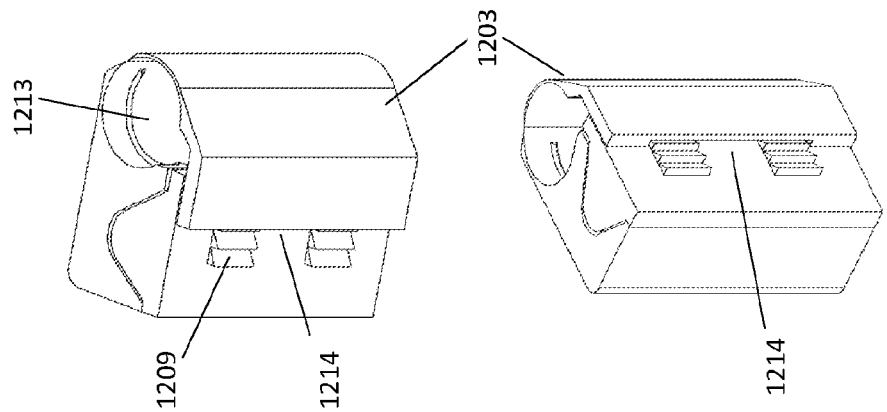
FIGS. 12a to 12c show an embodiment of a bridle connector in accordance with the present invention.
Figure 12B:
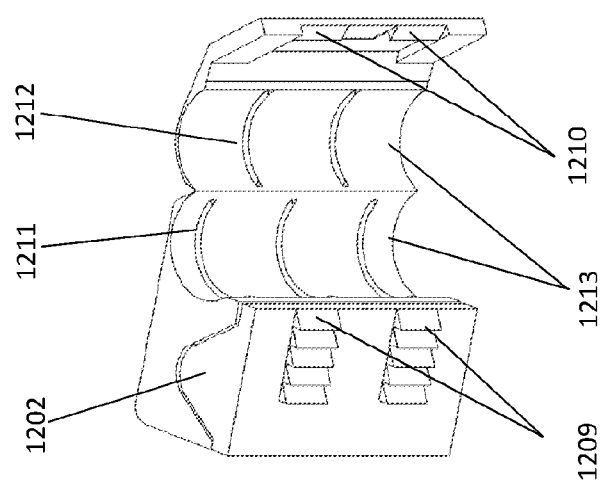
Figure 12A:
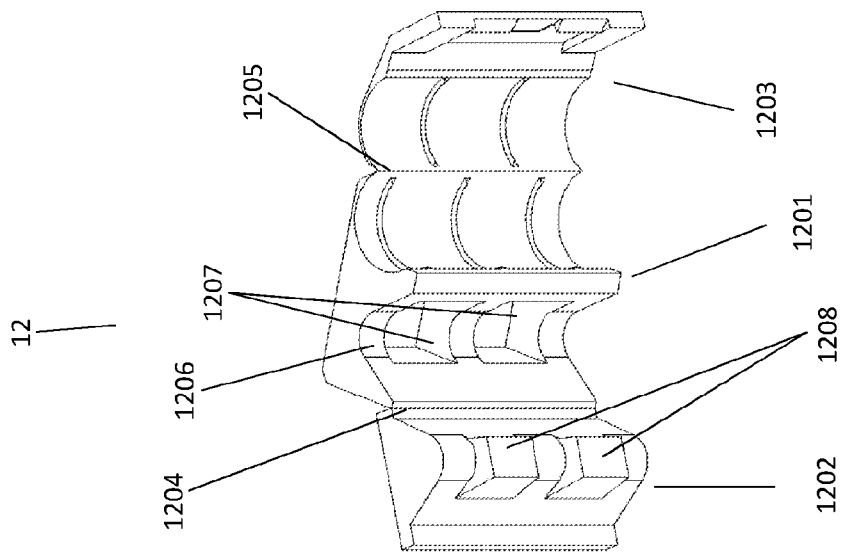

FIG. 12*a* shows a bridle connector 12 ready for use. The connector 12 comprises three parts, linked by two hinges. A central body 1201 is connected to a bridle tape retaining part 1202 by a first hinge 1204. A tube retaining part 1203 is joined to the central body 1201 by a second hinge 1205.

The hinges 1204, 1205 could be a conventional hinge, or a "living hinge". A living hinge is a common construction used in plastic parts, in which a thin area of plastic between two thicker parts creates a point of bending. This avoids the requirement to make and assemble separate parts.

The central body 1201 has a v-shaped feature 1206, which contains one or more cavities 1207. The bridle retaining part 1202 has one or more protrusions 1208, which correspond to the cavities and are arranged to lock into them when the bridle retaining part 1202 is closed. To hold the tape, the ends of the bridle tape are laid into the v-shaped feature 1206 and the bridle tape retaining part 1202 is closed.

The fit of the parts is arranged such that once the bridle retaining part 1202 is closed into the central body, it will not open, and so the join can be considered permanent. Once the bridle retaining part 1202 is closed therefore, the bridle can be removed from the nose only by cutting the bridle tape 10. This retention can be achieved with a tight fit, as shown, or with additional clip features. For example, the protrusions 1208 or cavities 1207 may include keying features, such as ribs or short pins (not shown) to provide a better grip to the bridle tape, and to prevent it pulling through once the bridle retaining part is closed.

FIG. 12*b* shows the bridle connector 12 with the bridle retaining part 1202 closed, as it would be when attached to the two ends of bridle tape. The tube retaining part 1203 is open, ready to attach a feeding tube.

The central body 1201 and tube retaining part 1203 both include tube-shaped portions 1213 are formed within. These 1213 fit to the outside diameter of a feeding tube when the tube retaining part 1203 is closed. The tube-shaped portions 1213 also include one or more grip features 1211 and 2112. These are arranged to dig slightly into the tube when the tube retaining part 1203 is closed. This makes it possible to grip the tube uniformly regardless of normal variation of tube diameter.

One or more sets of teeth 1209 are provided on the back of the bridle tape retaining part 1202, with one or more corresponding teeth 1210 on the tube retaining part. When the tube retaining part 1203 is closed, the teeth 1209, 1210 interlock, and enable the connector 12 to hold the tube in place. The additional teeth 1209, 1210 provide a mechanism to close the opening 1213 more tightly and to allow it to accommodate smaller sizes of tubes. The teeth are spaced specifically for use with tube sizes known to be accommodated by the bridle connector.

FIG. 12*c* shows two views of the bridle connector 12 with the tube retaining part 1203 closed, as it would be when attached to a nasal bridle and holding a feeding tube in opening 1213.

An opening 1214 allows a tool to be inserted to disengage the teeth 1209, 1210 and open the tube retaining part 1203, without disturbing the connection to the nasal bridle. The tool could be a key. This enables the tube retaining part 1203 to be opened. If the feeding tube needs to be changed, for example, if it became blocked, then this feature allows the connector to be disconnected from the tube, permitting its replacement, without having to remove the nasal bridle.

In alternative embodiments of the invention, markings may be affixed to the insertion guide to show how far it has been inserted. Markings could also, or alternatively, be made on the introducer, extending from the point where it meets the clip body in FIG. 8. Such markings would provide an indication of how far the introducer is protruding from the insertion guide.

Terminology

Nasal bridle—a bridle tape looped over (i.e. behind) the septum, with the ends protruding from respective nostrils, the ends joined with a bridle connector to a feeding tube to prevent the tube's removal.

Nasal bridle insertion device—the whole device for inserting a nasal bridle—threading bridle tape up one nostril, behind the septum and out of the opposite nostril.

Insertion guide—an item inserted in one nostril to guide the introducer through a "U-turn" over the back of the septum so that it is diverted down the opposite nostril.

Introducer—length of material that can be inserted along the insertion guide, with bridle tape attached to one end. The introducer should be sufficiently stiff to be pushed along the insertion guide, and to find its way down the opposite nostril, but also sufficiently flexible to bend round the insertion guide, not to cause trauma and to find its way round bends in its path. The introducer is then used to pull the bridle tape through to follow it.

Bridle tape—the string, cord, tube, surgical tape or similar to be looped over the septum, making up the bridle once the insertion guide and introducer are removed.

Bridle connector—an item used to connect to the two ends of the bridle tape protruding from each nostril after insertion, and able to attach to one or more feeding tubes in such a way as to prevent or to reduce the possibility of the feeding tube being inadvertently pulled out.

REFERENCES

Gupta P. K, Fitchett J, Simmons J, De Silva A. N. Efficacy of nasal bridles in preventing nasogastric tube displacement. The Royal Berkshire experience. Gastroenterology, 2010. 138 SUPPL; 1: S234-S235.

NPSA. Patient Safety Alert NPSA/2011/PSA002: Reducing the harm caused by misplaced nasogastric feeding tubes in adults, children and infants. Supporting Information. March 2011.

Seder C W, Stockdale W, Hale L, Janczyk R J. Nasal bridling decreases feeding tube dislodgment and may increase caloric intake in the surgical intensive care unit: a randomized, controlled trial. Critical Care Medicine. 2010; 38:797-801.

Sorokin R, Gottlieb J E. Enhancing patient safety during feeding tube insertion. A review of more than 2000 insertions. Journal of Parenteral and Enteral Nutrition. 2006; 30:440-5.

Sparks D A, Chase D M, Coughlin L M, Perry E. Pulmonary Complications of 9931 Narrow-Bore Nasoenteric Tubes During Blind Placement: A Critical Review. Journal of Parenteral and Enteral Nutrition. 2011; 35:625-629.

Taylor S J. Confirming nasogastric feeding tube position versus the need to feed. Intensive and Critical Care Nursing. 2013; 29: 59-69.

Taylor S J, Allan K, McWilliam H, Brown J, Manara A. Equivalence of electromagnetic tracing (Cortrak) to X-ray in confirming position of nasogastric tube position. 2014. Submitted for journal review.

Taylor S J. Cortrak tube placement: Advanced training. 2014. Silhouette Publications. UK. http://www.nutrition-support.info/. ISBN: 978-0-9574558-3-2

The invention claimed is:

1. A nasal bridle insertion device including: an elongated insertion guide made of flexible resilient material of a size suitable for insertion in a nasal passage, the guide being switchable between an insertion configuration and an introduction configuration, and comprising an internal lumen extending along the guide to an exit aperture at a distal end of a tip portion, and an introducer comprising a bendable, elongate body having a smooth shape on a leading end thereof and a low-profile join to a length of bridle tape at a trailing end thereof;

the smooth shape having a diameter that is larger than the exit aperture;

wherein the introducer is fitted within the internal lumen of the guide with the smooth shape protruding from the exit aperture;

when the guide is arranged in the insertion configuration, the tip portion is substantially straight, in line with a longitudinal axis of the guide; and when the guide is arranged in the introduction configuration, the tip portion is hook-shaped such that the internal lumen provides a channel through the tip portion to the exit aperture at its distal end, the exit aperture thereby being displaced laterally from the longitudinal axis of the guide; such that when the guide with the fitted introducer is inserted in a first nasal passage such that the exit aperture is positioned above a nasal septum, adoption of the introduction configuration results in the channel and the fitted introducer extending around the nasal septum into a second nasal passage, whereby the introducer exiting the exit aperture is guided above and beyond the septum and directly enters the second nasal passage.

2. The device according to claim 1 wherein one side of the tip portion includes one or more wedged slits and a tensionable actuation lead attached to the same side of the tip portion at or beyond the one or more slits, such that tensioning the actuation lead closes the one or more slits, causing the tip portion to adopt the hook shape.

3. The device according to claim 2 wherein the guide comprises two parts: an upper flexible end, which includes the tip portion, and a lower shaft portion, the upper flexible end being fabricated from a softer, more flexible material than the lower shaft portion.

4. The device according to claim 3 wherein the upper flexible end is fabricated from a thermoplastic elastomer, a thermoplastic polyurethane material, rubber or low-density polyethylene.

5. The device according to claim 3 wherein the lower shaft portion is fabricated from a thermoplastic elastomer, polypropylene, polyethylene or other similar plastic.

6. The device according to claim 3, further comprising an actuator switch with a clip connected to the actuation lead, wherein the clip is moveable between a first position in which the actuation lead is substantially free from tension and a second position in which the actuation lead is under tension, the tension being sufficient to cause the tip portion to adopt the hook shape.

7. The device according to claim 6 wherein the clip is moveable through a range of positions, each of which imparts a different tension to the actuation lead, thereby enabling selection of a range of introduction configurations.

8. The device according to claim 6 wherein the actuator switch is affixed to a proximal end of the guide, remote from the tip portion.

9. The device according to claim 8 wherein the actuator switch includes a passage which is substantially in line with the internal lumen of the guide through which the introducer is configured to pass.

10. The device according to claim 8 wherein the actuator switch includes a housing for the clip, the housing extending to a side of the guide opposite a side of the guide that includes the exit aperture, thereby providing an indication of exit aperture orientation.

11. The device according to claim 2 wherein the guide includes an orientation indicator extending radially outwardly from a position in the vicinity of a lower end of the guide in a direction opposite to a side of the guide that includes the exit aperture, thereby providing an indication of exit aperture orientation.

12. The device according to claim 1, wherein the elongate body of the introducer comprises a coiled spring and the smooth shape on its leading end is a sphere.

13. The device according to claim 1 wherein the device also includes a clip, the clip comprising a central body, a bridle tape retaining part and a tube retaining part, wherein the central body and the bridle tape retaining part include complementary cavities and protrusions adapted to retain the length of bridle tape and the central body and the tube retaining part include tube-shaped portions, the tube retaining part also including teeth adapted to releasably lock to corresponding teeth elsewhere on the clip when a tube is retained.

14. A method of inserting a nasal bridle into a nose, the method comprising:
  (a) fitting an introducer comprising a bendable, elongate body having a smooth shape with a diameter on its leading end and a low-profile join to a length of bridle tape at its trailing end into an internal lumen of an elongated insertion guide, the guide being made of flexible resilient material with a tip portion that includes an exit aperture at its distal end, such that the diameter of the smooth shape is larger than the exit aperture and the smooth shape protrudes from the guide,
  (b) inserting the guide with the fitted introducer into a first nasal passage, the guide being in an insertion configuration in which the tip portion is substantially straight, in line with a longitudinal axis of the guide, until the exit aperture is positioned above a septum of the nose;
  (c) switching the guide, in situ, to an introduction configuration wherein the tip portion is hook-shaped, the exit aperture thereby being laterally displaced from the longitudinal axis, and whereby the internal lumen provides a channel through the tip portion that extends around the septum to the exit aperture in a second nasal passage;
  (d) pushing the introducer through the channel and out of the exit aperture such that the introducer is directed above and beyond the septum directly into the second nasal passage until the introducer emerges from the second nasal passage;
  (e) pulling the introducer out through the second nasal passage until the bridle tape emerges; and
  (f) reverting the guide to its insertion configuration and removing it from the first nasal passage.

15. The method of claim 14 wherein the bridle tape has two ends, the method further comprising an additional step after step (f) of fitting a bridle connector to the two ends of the bridle tape and cutting off any excess tape.

* * * * *